US012653601B2

(12) United States Patent
Widenhouse et al.

(10) Patent No.: US 12,653,601 B2
(45) Date of Patent: Jun. 16, 2026

---

(54) PERICARDIOTOMY DEVICES AND RELATED METHODS

(71) Applicant: AtriCure, Inc., Mason, OH (US)

(72) Inventors: Christopher Widenhouse, Mason, OH (US); Jacob Luisi, Cincinnati, OH (US); Rachel Lauren Budke, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 965 days.

(21) Appl. No.: 17/588,226

(22) Filed: Jan. 29, 2022

(65) Prior Publication Data

US 2023/0200880 A1 Jun. 29, 2023

Related U.S. Application Data

(60) Provisional application No. 63/294,454, filed on Dec. 29, 2021.

(51) Int. Cl.
*A61B 18/12* (2006.01)
*A61B 18/16* (2006.01)
*A61B 18/00* (2006.01)

(52) U.S. Cl.
CPC .......... *A61B 18/1233* (2013.01); *A61B 18/16* (2013.01); *A61B 2018/00363* (2013.01);
(Continued)

(58) Field of Classification Search
CPC ............ A61B 18/1206; A61B 18/1233; A61B 18/1482; A61B 18/16; A61B 2018/00291;
(Continued)

(56) References Cited

U.S. PATENT DOCUMENTS

| | | | |
|---|---|---|---|
| 5,336,252 A | 8/1994 | Cohen | |
| 5,972,013 A | 10/1999 | Schmidt | |

(Continued)

FOREIGN PATENT DOCUMENTS

| | | |
|---|---|---|
| EP | 3066999 | 9/2016 |
| WO | 2004078066 | 9/2004 |

(Continued)

OTHER PUBLICATIONS

Kumar et al., "Needle-in-needle" epicardial access: Preliminary observations with a modified technique for facilitating epicardial interventional procedures, Heart Rhythm, vol. 12, No. 7, pp. 1691-1697, Jul. 2015.

(Continued)

*Primary Examiner* — Tigist S Demie
(74) *Attorney, Agent, or Firm* — Dorton & Willis LLP; Ryan Willis

(57) ABSTRACT

Electrosurgical pericardiotomy devices are disclosed. An example electrosurgical pericardiotomy device configured to create an opening through a pericardium may include an end effector comprising a tip portion and at least one electrosurgical electrode. The tip portion may include an opening configured to engage a target portion of a pericardium, and the tip portion may be configured, upon application of vacuum to the tip portion, to separate the target portion of the pericardium from an external surface of a heart. The electrosurgical electrode may be disposed proximate the tip portion so that, with vacuum applied to the tip portion, the target portion of the pericardium contacts the electrosurgical electrode. The electrosurgical electrode may be configured to create an opening through the target portion of the pericardium using electrosurgical energy.

18 Claims, 16 Drawing Sheets

(52) U.S. Cl.
CPC ............... *A61B 2018/00577* (2013.01); *A61B 2018/1253* (2013.01); *A61B 2018/126* (2013.01); *A61B 2218/007* (2013.01)

(58) Field of Classification Search
CPC   A61B 2018/00363; A61B 2018/00577; A61B 2018/00601; A61B 2018/1253; A61B 2018/126; A61B 2018/142; A61B 2218/007
See application file for complete search history.

(56) References Cited

U.S. PATENT DOCUMENTS

| | | | |
|---|---|---|---|
| 6,231,518 | B1 | 5/2001 | Grabek et al. |
| 6,592,552 | B1 | 7/2003 | Schmidt |
| 6,890,295 | B2 | 5/2005 | Michels et al. |
| 6,918,890 | B2 | 7/2005 | Schmidt |
| 8,308,720 | B2 * | 11/2012 | Davies ............... A61B 18/1492 |
| | | | 606/41 |
| 8,986,278 | B2 | 3/2015 | Fung et al. |
| 2002/0128602 | A1 | 9/2002 | Adams et al. |
| 2004/0167558 | A1 | 8/2004 | Igo et al. |
| 2007/0135686 | A1 | 6/2007 | Pruitt, Jr. et al. |
| 2008/0009747 | A1 * | 1/2008 | Saadat ..................... A61B 1/04 |
| | | | 604/510 |
| 2008/0306333 | A1 | 12/2008 | Chin |
| 2010/0145306 | A1 | 6/2010 | Mickley et al. |
| 2010/0160719 | A1 | 6/2010 | Kassab et al. |
| 2010/0280316 | A1 | 11/2010 | Dietz et al. |
| 2012/0095434 | A1 | 4/2012 | Fung et al. |
| 2013/0046305 | A1 * | 2/2013 | Davies ............... A61B 18/1492 |
| | | | 606/45 |
| 2015/0258270 | A1 * | 9/2015 | Kunis ..................... A61M 5/00 |
| | | | 604/506 |
| 2015/0359558 | A1 | 12/2015 | Kardosh et al. |
| 2016/0081735 | A1 | 3/2016 | Kassab et al. |
| 2021/0008338 | A1 | 1/2021 | Morejohn et al. |
| 2023/0039545 | A1 * | 2/2023 | Greeley ............. A61B 18/1487 |

FOREIGN PATENT DOCUMENTS

| | | |
|---|---|---|
| WO | 2007120775 | 10/2007 |
| WO | 2017139463 | 8/2017 |
| WO | 2018148456 | 8/2018 |
| WO | 2020/014193 | 1/2020 |
| WO | 2023/129658 | 7/2023 |

OTHER PUBLICATIONS

CONMED Corporation, PenAdapt® Surgical Smoke Evacuation Adapter product brochure, 2 pages, 2019.
Wikipedia.org, Veress needle, retrieved from https://en.wikipedia.org/wiki/Veress_needle on Sep. 28, 2021.
Medtronic, LigaSure TM Small Jaw Open Sealer/Divider, retrieved from https://www.medtronic.com/covidien/en-us/products/vessel-sealing/ligasure-small-jaw.html on Sep. 28, 2021.
Symmetry Surgical Inc., Energy Solutions catalog, 72 pages, 2021.

* cited by examiner

700

706

710

800

807

806

14

808

PERICARDIOTOMY DEVICES AND RELATED METHODS

CROSS REFERENCE TO RELATED APPLICATIONS

This application claims the benefit of U.S. Provisional Application No. 62/294,454, filed Dec. 29, 2021, which is incorporated by reference.

INTRODUCTION TO THE INVENTION

The present disclosure is directed to medical instruments and devices and related methods, and, more specifically, to surgical devices for creating an opening in a pericardium, and related methods.

The present disclosure contemplates that some internal anatomic structures may be at least partially covered by one or more layers of tissue. For example, in mammals, the heart is partially surrounded by a sac-like tissue called the pericardium.

Further, the present disclosure contemplates that in connection with some surgical procedures, such as minimally invasive procedures (e.g., endoscopic procedures), it may be necessary to obtain access to such anatomic structures. For example, in connection with some cardiac procedures, it may be necessary to penetrate the pericardium to allow surgical instruments to directly access the heart. As used herein, "pericardiotomy" may refer to a surgical procedure in which an opening is created through a patient's pericardium. A pericardiotomy may be performed to allow a surgeon to access the patient's heart, such as in connection with cardiac ablation to treat atrial fibrillation and/or occlusion of the left atrial appendage.

The present disclosure contemplates that surgeons may encounter challenges when performing pericardiotomies, especially in connection with minimally invasive procedures. For example, it is generally desirable to create an opening through the pericardium without substantially affecting (e.g., cutting or burning) the underlying epicardium (i.e., the heart wall). Additionally, when a pericardiotomy is performed with the patient's heart beating (e.g., not on cardiopulmonary bypass), the movement of the heart and/or the pericardium may increase the complexity of the procedure.

While known devices and techniques have been used to perform pericardiotomies, improvements in the construction and operation of pericardiotomy devices is beneficial for users (e.g., surgeons) and patients. The present disclosure includes various improvements which may enhance the construction, operation, and methods of use of pericardiotomy devices.

It is an aspect of the present disclosure to provide an electrosurgical pericardiotomy device configured to create an opening through a pericardium. The electrosurgical pericardiotomy device may include an end effector including a tip portion including an opening configured to engage a target portion of a pericardium, wherein the tip portion is configured, upon application of vacuum to the tip portion, to separate the target portion of the pericardium from an external surface of a heart; and at least one electrosurgical electrode disposed proximate the tip portion so that, with vacuum applied to the tip portion, the target portion of the pericardium contacts the electrosurgical electrode. The electrosurgical electrode may be configured to create an opening through the target portion of the pericardium using electrosurgical energy delivered to the electrosurgical electrode.

In a detailed embodiment, the electrosurgical electrode may be recessed within the tip portion. The opening may include a distal opening and the electrosurgical electrode may be recessed proximally within the tip portion relative to the distal opening. The electrosurgical pericardiotomy device may include an elongated shaft, and the end effector may be disposed distally on the shaft. The electrosurgical pericardiotomy device may include a handle, and the handle may be disposed proximally on the shaft. The tip portion may be formed in a bell shape so that a proximal portion of the tip portion has an outer diameter approximately the same as an outer diameter of the shaft and a distal end of the tip portion has an outer diameter that is substantially greater than the outer diameter of the shaft. The outer diameter of the distal end of the tip portion may be about twice the outer diameter of the shaft.

In a detailed embodiment, the electrosurgical pericardiotomy may include at least one electrical connector electrically coupled to the electrosurgical electrode and configured to electrically connect to an electrosurgical generator. The electrosurgical pericardiotomy device may include at least one vacuum connector fluidically coupled to the tip portion and configured to fluidically connect to a vacuum source.

In some embodiments, the electrosurgical electrode may include a monopolar electrosurgical electrode configured for monopolar operation. The monopolar electrosurgical electrode may be configured to be utilized in connection with a return electrode positioned remotely from the monopolar electrosurgical electrode. In some embodiments, the electrosurgical electrode may include a pair of bipolar electrosurgical electrodes configured for cooperative bipolar operation.

In a detailed embodiment, the electrosurgical pericardiotomy device may include an off-the-shelf electrosurgical device electrical connector configured to electrically connect with an active electrode of an off-the-shelf electrosurgical device. The off-the-shelf electrosurgical device electrical connector may be electrically coupled to the electrosurgical electrode so that when the off-the-shelf electrosurgical device is activated, electrical energy is delivered to the electrode of the pericardiotomy device from an electrosurgical generator via the off-the-shelf electrosurgical device. In some embodiments, the off-the-shelf electrosurgical device may be configured for monopolar operation and the electrosurgical pericardiotomy device may be configured for monopolar operation. In some embodiments, the off-the-shelf electrosurgical device may be configured for monopolar operation and the electrosurgical pericardiotomy device may be configured for bipolar operation. In some such embodiments, the electrosurgical electrode may include a first electrode and a second electrode disposed proximate the tip portion and configured for bipolar operation, the off-the-shelf electrosurgical device electrical connector may be electrically coupled to the first electrode, the electrosurgical pericardiotomy device may include an electrical connector electrically coupled to the second electrode, and/or the electrical connector may be configured to be connected to a return electrode connection of the electrosurgical generator.

In a detailed embodiment, the electrosurgical electrode may include a first electrode and a second electrode disposed proximate the tip portion and configured for bipolar operation. The first electrode may be configured to be operatively coupled to a monopolar connection of an electrosurgical generator and/or the second electrode may be configured to be operatively coupled to a return electrode connection of the electrosurgical generator.

It is an aspect of the present disclosure to provide a method of creating an opening through a pericardium, including engaging an opening of a tip portion of an end effector of an electrosurgical pericardiotomy device with a pericardium, the end effector comprising the tip portion and at least one electrosurgical electrode disposed proximate the tip portion; separating a target portion of the pericardium from a heart by applying vacuum to the tip portion; contacting the electrosurgical electrode with the target portion of the pericardium; and/or creating an opening through the target portion of the pericardium by applying electrosurgical energy to the at least one electrosurgical electrode.

In a detailed embodiment, the at least one electrosurgical electrode may be recessed within the tip portion. Contacting the electrosurgical electrode of the electrosurgical pericar-diotomy device disposed proximate the tip portion with the target portion of the pericardium may include drawing the target portion of the pericardium into the tip portion. The opening may include a distal opening and the electrosurgical electrode may be recessed proximally within the tip portion relative to the distal opening. Drawing the target portion of the pericardium into the tip portion may include drawing the target portion of the pericardium proximally into the tip portion.

In a detailed embodiment, the method may include, before engaging the opening of the tip portion of the electrosurgical pericardiotomy device with the pericardium, positioning the tip portion proximate the pericardium. The electrosurgical pericardiotomy device may include an elongated shaft, and the end effector may be disposed distally on the shaft. Positioning the tip portion proximate the pericardium may include positioning the end effector using the shaft. The electrosurgical pericardiotomy device may include a handle disposed proximally on the shaft. Positioning the end effec-tor using the shaft may include positioning the shaft and the end effector using the handle.

In a detailed embodiment, the electrosurgical pericar-diotomy device may include at least one vacuum connector fluidically coupled to the tip portion. The method may include fluidically connecting the vacuum connector to a vacuum source.

In a detailed embodiment, the electrosurgical electrode may include a monopolar electrosurgical electrode config-ured for monopolar operation in connection with a return electrode positioned remotely from the monopolar electro-surgical electrode during use. Applying electrosurgical energy to the at least one electrosurgical electrode may include applying monopolar electrosurgical energy to the monopolar electrosurgical electrode.

In a detailed embodiment, the electrosurgical electrode may include a pair of bipolar electrosurgical electrodes configured for cooperative bipolar operation. Applying elec-trosurgical energy to the at least one electrosurgical elec-trode may include applying bipolar electrosurgical energy to the pair of bipolar electrosurgical electrodes.

In a detailed embodiment, the electrosurgical pericar-diotomy device may include at least one electrical connector electrically coupled to the electrosurgical electrode. The method may include electrically connecting the electrosur-gical electrode to an electrosurgical generator using the electrical connector. The method may include connecting a return electrode to the electrosurgical generator and/or posi-tioning the return electrode for use remotely from the pericardium.

In a detailed embodiment, the electrosurgical pericar-diotomy device may include an off-the-shelf electrosurgical device electrical connector configured to electrically connect with an active electrode of an off-the-shelf electrosur-gical device. The off-the-shelf electrosurgical device elec-trical connector may be electrically coupled to the electrosurgical electrode. The method may include electri-cally connecting the off-the-shelf electrosurgical device electrical connector with the active electrode of the off-the-shelf electrosurgical device and electrically connecting the off-the-shelf electrosurgical device to an electrosurgical gen-erator. Applying electrosurgical energy to the electrosurgical electrode may include delivering electrical energy to the electrosurgical electrode from the electrosurgical generator via the off-the shelf electrosurgical device.

In some embodiments, the off-the-shelf electrosurgical device may be configured for monopolar operation and/or the electrosurgical electrode may include a monopolar elec-trosurgical electrode configured for monopolar operation in connection with a return electrode positioned remotely from the monopolar electrosurgical electrode during use. Deliv-ering electrical energy to the electrosurgical electrode from the electrosurgical generator via the off-the shelf electrosur-gical device may include delivering electrical energy from the electrosurgical generator via the off-the-shelf electrosur-gical device to the monopolar electrosurgical electrode.

In some embodiments, the off-the-shelf electrosurgical device may be configured for monopolar operation and/or the electrosurgical electrode may include a pair of bipolar electrosurgical electrodes configured for cooperative bipolar operation, the pair of bipolar electrosurgical electrodes com-prising a first electrode and a second electrode. Delivering electrical energy to the electrosurgical electrode from the electrosurgical generator via the off-the shelf electrosurgical device comprises delivering electrical energy from the elec-trosurgical generator via the off-the-shelf electrosurgical device to the first electrode. The electrosurgical pericar-diotomy device may include an electrical connector electri-cally coupled to the second electrode and/or the method may include electrically connecting the electrical connector to a return electrode connection of the electrosurgical generator.

It is an aspect of the present disclosure to provide a method of creating an opening through a pericardium, including applying suction to an opening of an end effector of an electrosurgical pericardiotomy device, where the end effector includes an electrosurgical electrode disposed proxi-mate the opening, while the end effector is proximate a pericardium to draw the pericardium toward the opening; increasing a distance between a target portion of the peri-cardium and an exterior surface of a heart to effectuate an ablation spacing by applying suction to the pericardium; contacting the target portion of the pericardium with the electrosurgical electrode while the ablation spacing is main-tained; and/or ablating the target portion of the pericardium to create an opening therethrough by applying energy to the electrosurgical electrode while the target portion of the pericardium contacts the electrosurgical electrode.

In a detailed embodiment, the electrosurgical pericar-diotomy device may include an off-the-shelf electrosurgical device electrical connector configured to electrically con-nect with an active electrode of an off-the-shelf electrosur-gical device, the off-the-shelf electrosurgical device electri-cal connector electrically coupled to the electrosurgical electrode. The method may include electrically connecting the off-the-shelf electrosurgical device electrical connector with the active electrode of the off-the-shelf electrosurgical device and electrically connecting the off-the-shelf electro-surgical device to an electrosurgical generator. Applying energy to the electrosurgical electrode may include delivering electrical energy to the electrosurgical electrode from the electrosurgical generator via the off-the shelf electrosurgical device.

In a detailed embodiment, the opening may include a distal opening and the electrosurgical electrode may be recessed proximally within the end effector relative to the distal opening. Increasing the distance between the target portion of the pericardium and the exterior surface of the heart may include drawing the target portion of the pericardium proximally into the end effector.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating medical and surgical procedures, such as for creating an opening through a pericardium. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure. Unless explicitly stated otherwise, any feature or function described in connection with any example embodiment may be utilized with features or functions described in connection with other example embodiments. Repeated description of similar features and functions is omitted for brevity.

Figure 1:
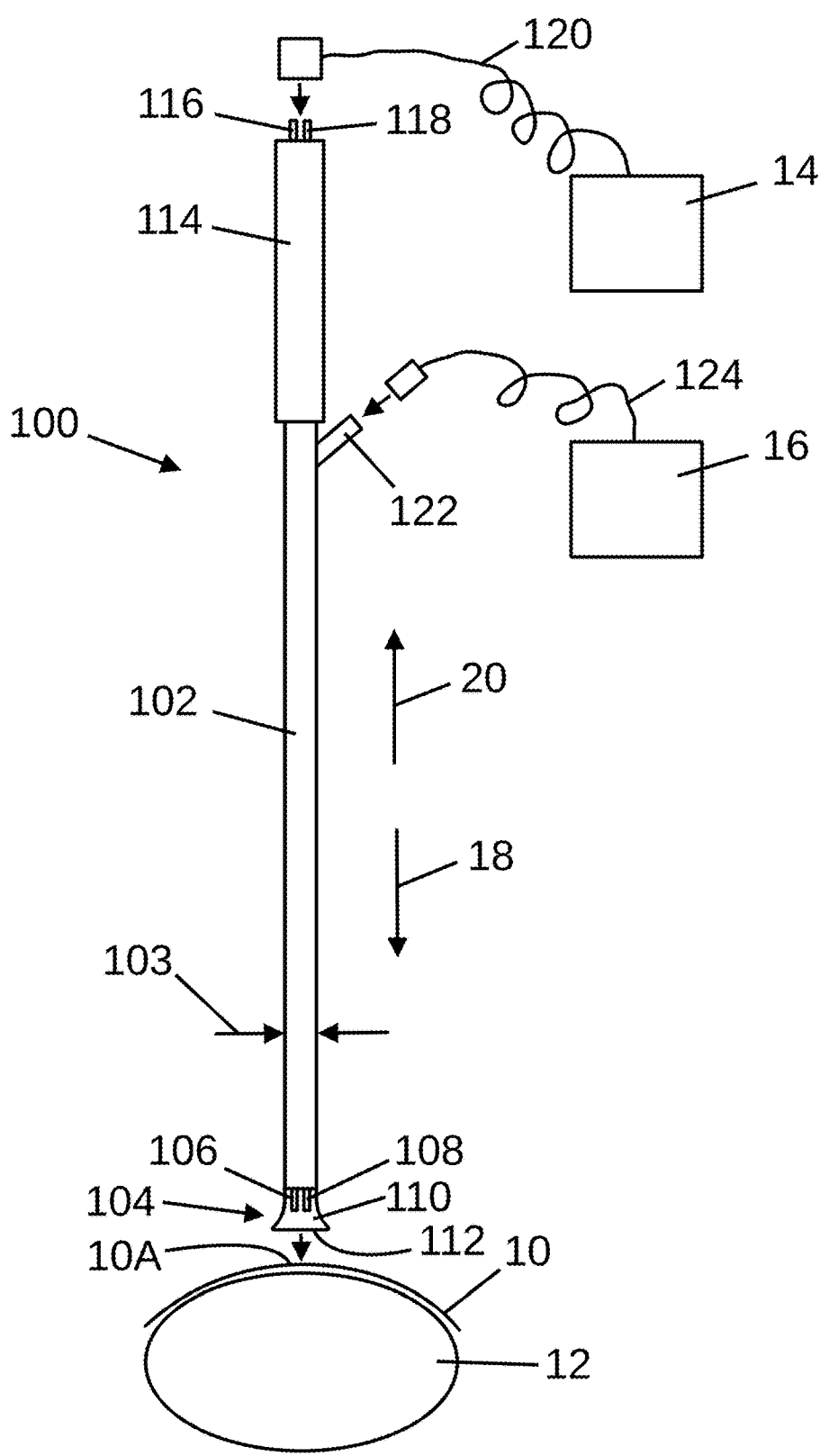
FIG. 1 is a simplified schematic view of an example bipolar electrosurgical pericardiotomy device.

FIG. 1 is a simplified schematic view of an example bipolar electrosurgical pericardiotomy device 100 according to at least some aspects of the present disclosure. The pericardiotomy device 100 may be used in connection with a pericardiotomy procedure including creating an opening through a patient's pericardium 10, such as to obtain access to the patient's heart 12. The pericardiotomy device 100 may be operatively coupled to an electrosurgical generator 14 and/or a vacuum source 16.

For clarity, the following description references a distal direction 18 and a proximal direction 20. The proximal direction 20 may be generally opposite the distal direction 18. As used herein, "distal" may refer to a direction generally away from an operator of a system or device (e.g., a surgeon), such as toward the distant-most end of a device that is inserted into a patient's body. As used herein, "proximal" may refer to a direction generally toward an operator of a system or device (e.g., a surgeon), such as away from the distant-most end of a device that is inserted into a patient's body. It will be understood, however, that example directions referenced herein are merely for purposes of explanation and clarity, and should not be considered limiting.

In the illustrated embodiment, the pericardiotomy device 100 includes an elongated, generally tubular shaft 102 and an end effector 104 disposed generally distally on the shaft 102. In some example embodiments, the shaft 102 may have an outer diameter 103 of about 5.0 mm. The shaft 102 may be configured to be substantially rigid, elastically deformable, and/or plastically deformable (when subject to forces consistent with normal, intended use of the device 100), and such characteristics may vary over the shaft's 102 proximal-distal length.

In the illustrated embodiment, the end effector 104 includes one or more electrodes 106, 108 configured to be placed into contact with the pericardium 10. Electrical energy from the electrosurgical generator 14 may be selectively supplied to the electrosurgical electrodes 106, 108 to cause the electrodes 106, 108 to create an opening through the pericardium 10.

In the illustrated embodiment, the end effector 104 includes a tip portion 110. The electrodes 106, 108 may be disposed at least partially within the tip portion 110. The tip portion 110 may include an opening, such as a distal opening 112, configured to engage the pericardium 10 and allow the pericardium to contact the electrodes 106, 108. In some alternative embodiments, the opening may be oriented in another direction, such as generally laterally. In some example embodiments, the distal opening 112 may be generally circular. In some alternative embodiments, the opening may have another shape, such as a generally elongated channel. Vacuum from the vacuum source 16 may be selectively applied to the tip portion 110, such as to separate and/or increase spacing between a target portion 10A of the pericardium 10 from an external surface of the heart 12 and/or to draw the target portion 10A of the pericardium 10 into contact with the electrodes 106, 108. In some example embodiments, the tip portion 110 may be constructed from a substantially transparent material (e.g., a substantially optically clear material), which may facilitate visibility through the tip portion 110, such as visualization of the electrodes 106, 108. In other embodiments, at least a portion of the tip portion 110 may be constructed at least partially of a translucent material and/or an opaque material such as, without limitation, a radiopaque material.

In the illustrated embodiment, the pericardiotomy device 100 includes a handle 114 disposed proximally on the shaft 102. The handle 114 may be configured to be grasped by a user (e.g., surgeon) and/or a robotic device (e.g., a surgical robot). More generally, the handle 114 may comprise any structure that may be configured to be secured, held, and/or manipulated to position or restrain the pericardiotomy device 100, regardless of whether it may be utilized by a human (e.g., surgeon or assistant), robot, mechanical device, etc.

The pericardiotomy device 100 may include one or more electrical connectors 116, 118, which may be used to electrically connect the pericardiotomy device 100 to the electrosurgical generator 14. In the illustrated embodiment, the electrical connectors 116, 118 are disposed on the handle 114 and are configured to couple with an electrical cord 120 including one or more conductors. In other embodiments, the cord 120 may extend from the pericardiotomy device 100, and the electrical connectors 116, 118 may be disposed on the end of the cord 120 that attaches to the electrosurgical generator 14. (See, for example, FIG. 5.) In still further embodiments, the cord 120 and/or electrosurgical generator 14 may be incorporated into the handle 114 or permanently attached thereto.

The pericardiotomy device 100 may include at least one vacuum connector 122, which may be used to fluidically connect the pericardiotomy device 100 to the vacuum source 16. In the illustrated embodiment, the vacuum connector 122 is disposed generally proximally on the shaft 102 near the handle 114, and the vacuum connector 122 is configured to couple with a vacuum line 124 including one or more lumens. In other embodiments, the vacuum line 124 may extend from the pericardiotomy device 100, and the vacuum connector 122 may be disposed on the end of the line 124 that attaches to the vacuum source 16. (See, for example, FIG. 5.) Example vacuum sources 16 include vacuum pumps and connections to central vacuum systems, such as may be available in a hospital or surgical facility.

Figure 2:
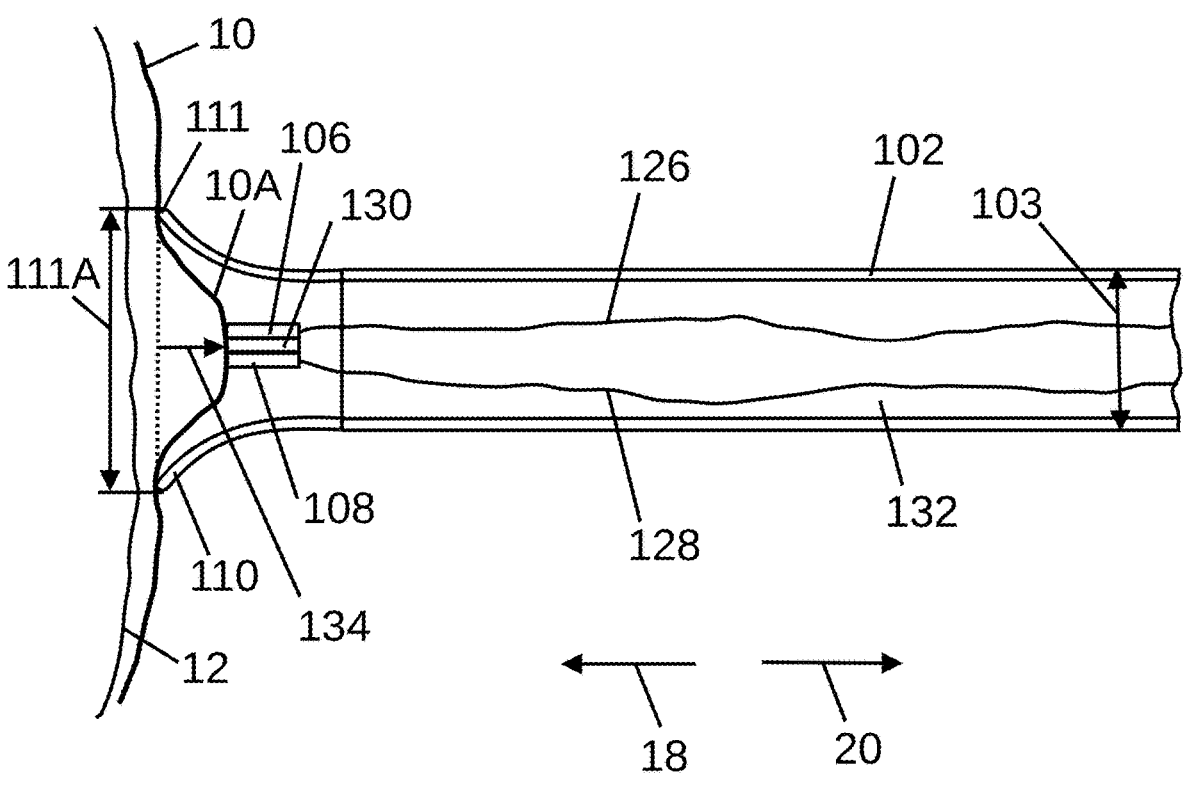
FIG. 2 is a simplified lateral cutaway view of a distal portion of the electrosurgical pericardiotomy device of FIG. 1.
Figure 3:
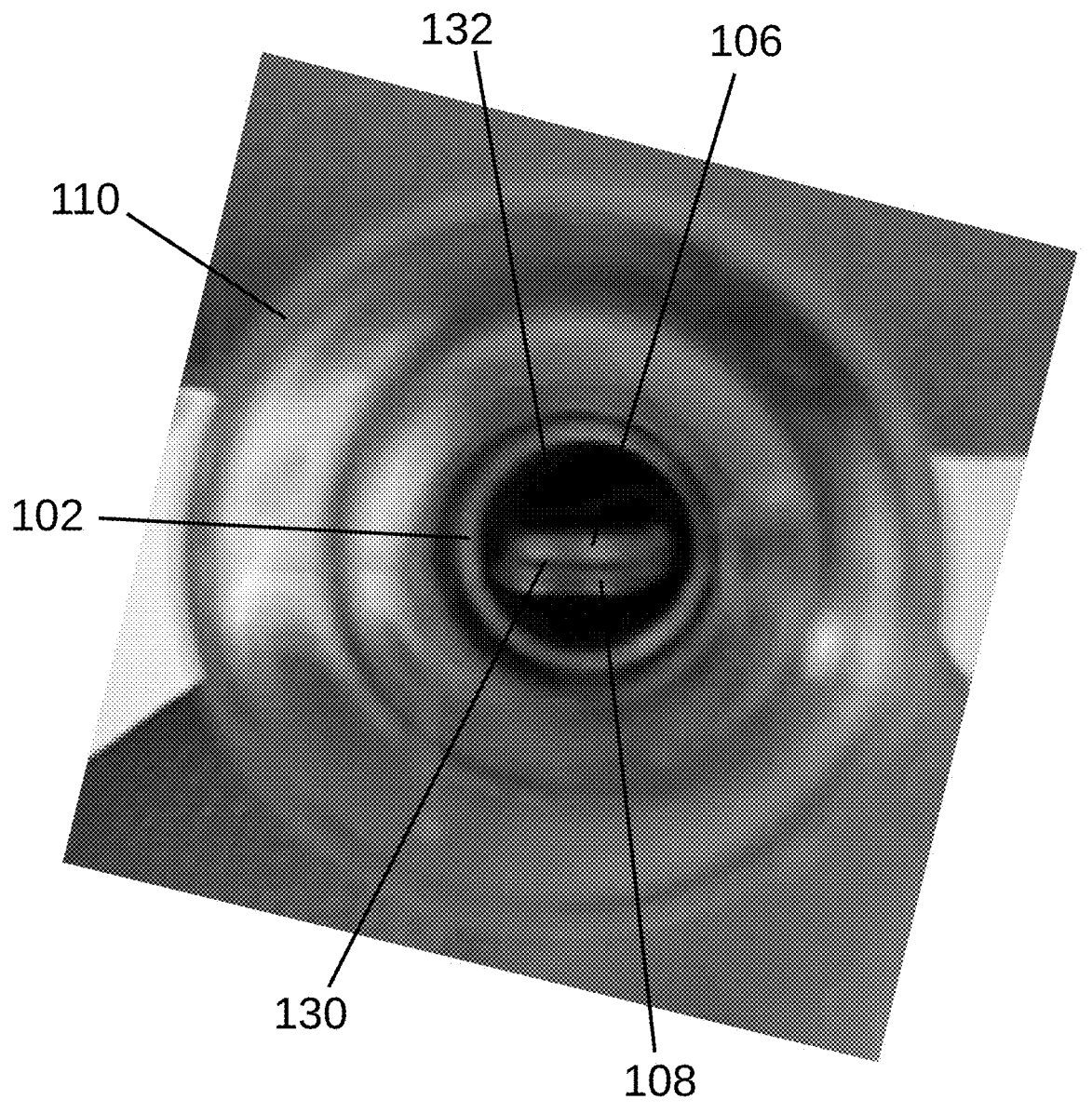
FIG. 3 is a detailed distal end view of the distal portion of the electrosurgical pericardiotomy device of FIG. 1.

FIG. 2 is a simplified lateral cutaway view of a distal portion of the electrosurgical pericardiotomy device 100 and FIG. 3 is a detailed distal end view of the distal portion of the electrosurgical pericardiotomy device 100, all according to at least some aspects of the present disclosure. Referring to FIG. 2, in the illustrated embodiment, the electrosurgical pericardiotomy device 100 includes one or more electrical conductors 126, 128, which electrically connect the electrodes 106, 108 to respective electrical connectors 116, 118 (FIG. 1). The electrical conductors 126, 128 may extend proximally within the shaft 102 from proximate the electrodes 106, 108 to proximate the electrical connectors 116, 118. Referring to FIGS. 2 and 3, in the illustrated embodiment, the electrodes 106, 108 may be configured in the form of a double blade electrode. Specifically, the electrodes 106, 108 may be disposed generally in parallel and may be at least partially interposed by an insulator 130. Referring to FIG. 3, in the illustrated embodiment, the electrodes 106, 108 are arranged generally diametrically with respect to the shaft 120. Referring to FIG. 2, in the illustrated embodiment, the electrodes 106, 108 are configured to direct electrical energy into the target portion 10A of the pericardium 10 in the vicinity of the electrodes 106, 108.

Referring to FIG. 2, in the illustrated embodiment, the electrodes 106, 108 are recessed proximally within the tip portion 110 at a distance shown by arrow 134. In other embodiments, the electrodes 106, 108 may be disposed at other proximal-distal positions within the tip portion 110, such as substantially even with the distal end of the tip portion 110 (e.g., zero distance recess). In yet other embodiments, the electrodes 106, 108 may be selectively repositionable in the distal 20 and proximal 18 directions to vary the proximal-distal positions within the tip portion 110.

Referring to FIG. 2, in the illustrated embodiment, at least a portion of the shaft 102 may at least partially define an internal channel 132. The channel 132 may be configured as a vacuum conduit fluidically interposing the tip portion 110 and the vacuum connector 122 (FIG. 1). Application of vacuum to the tip 110 (e.g., via the vacuum connector 122 and the internal channel 132) may be operative to draw the target portion 10A of the pericardium 10 into the tip portion 110 as illustrated by arrow 134. In this embodiment, drawing the target portion 10A of the pericardium 10 into the tip portion 110 by application of vacuum pulls the pericardium 10 into contact with the electrodes 106, 108. In the illustrated embodiment, because the electrodes 106, 108 are recessed proximally within the tip portion 110, drawing the pericardium 10 proximally into the tip portion 110 by application of vacuum also creates and/or increases the distance between the surface of the heart 12 and the location where electrical energy is applied to the pericardium 10 by the electrodes 106, 108. Thus, the likelihood of injury to the heart 12 (e.g., due to energy delivered by the electrodes 106, 108) may be reduced.

Referring to FIG. 2, in the illustrated embodiment, the tip portion 110 may be formed in a wide bell shape. For example, the proximal portion of the tip portion 110 may have an outer diameter approximately the same as the outer diameter 103 of the shaft 102 (e.g., about 5.0 mm). The distal end 111 of the tip portion 110 may have an outer diameter 111A that is substantially greater than the outer diameter 103 of the shaft 102. In some embodiments, the radially outer surface of the tip portion 110 may continuously curve, such as in a generally concave manner, between the proximal portion of the tip portion 110 near the shaft 102 and the distal end 111 of the tip portion 110. For example, the maximum outer diameter 111A of the tip portion 110

(e.g., proximate the distal end 111) may be about 10.0 mm. Thus, in some embodiments, the maximum outer diameter 111A of the tip portion 110 may be about twice the outer diameter 103 of the shaft 102.

Figure 4:
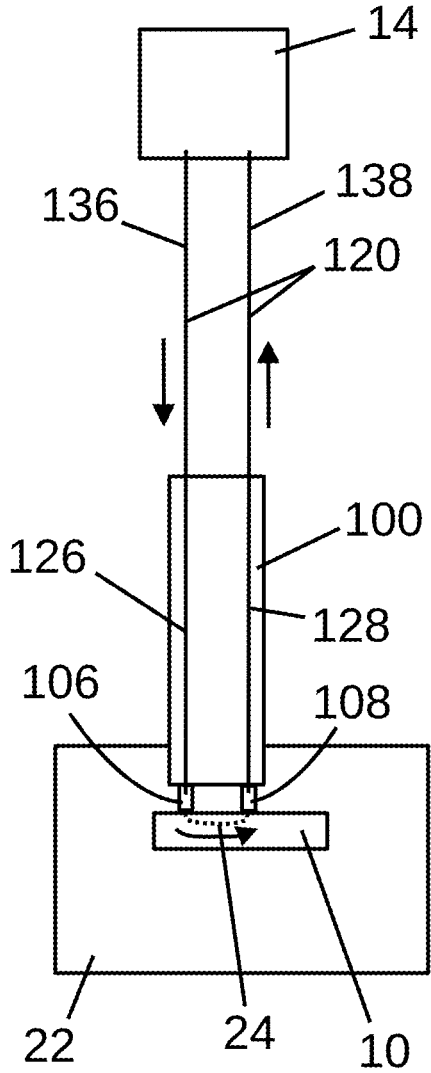
FIG. 4 is a simplified block diagram illustrating example bipolar operation of the pericardiotomy device of FIG. 1.

FIG. 4 is a simplified block diagram illustrating example bipolar operation of the pericardiotomy device 100, according to at least some aspects of the present disclosure. As used herein, "bipolar" may refer to an electrosurgical device configuration in which both of a cooperating pair of electrodes are disposed substantially at a surgical site during use. It will be understood that the electrosurgical generator 14 may supply direct current and/or alternating current of any suitable magnitude at any suitable voltage and in any suitable waveform (e.g., square wave, sine wave, etc.). However, for clarity, FIG. 4 illustrates current flow in one direction. It will be understood that various other embodiments described herein as having a bipolar configuration may be arranged and operated in a generally similar manner.

Referring to FIG. 4, electrical energy flows from the electrosurgical generator 14, through one electrically conductive line 136 forming part of the cord 120 to the electrosurgical pericardiotomy device 100. In particular, the electrical energy flows through the electrical conductor 126 to the first electrode 106. From the first electrode 106, the electrical energy flows through the target tissue (e.g., the pericardium 10) to the second electrode 108. Generally, the electrical energy remains within the target tissue (e.g., the pericardium 10) and has minimal or no effects on, and does not flow through (or minimally flows through), other portions of the patient's body 22. From the second electrode 108, the electrical energy flows through the electrical conductor 128 and another electrically conductive line 138 forming part of the cord 120 to the electrosurgical generator 14. In the illustrated bipolar configuration, the electrosurgical effect of the electrodes 106, 108 is applied substantially in the vicinity of the location 24 where the electrical energy flows through the target tissue (e.g., at the surgical site). The electrical energy ablates the target tissue at the surgical site, thereby creating an opening through the pericardium 10. In one example embodiment, the electrodes 106, 108 may be about 2.3 mm long, and the resulting opening may be about 2.3 mm long. The opening may be generally oval or generally circular in shape, for example. If a larger opening is desired, the electrodes 106, 108 may be repositioned and reactivated to create a larger opening. Alternatively, the opening may be expanded using surgical instruments, such as by using a grasper to pull the pericardium away from the heart and expanding the opening with scissors or electrocautery.

Figure 5:
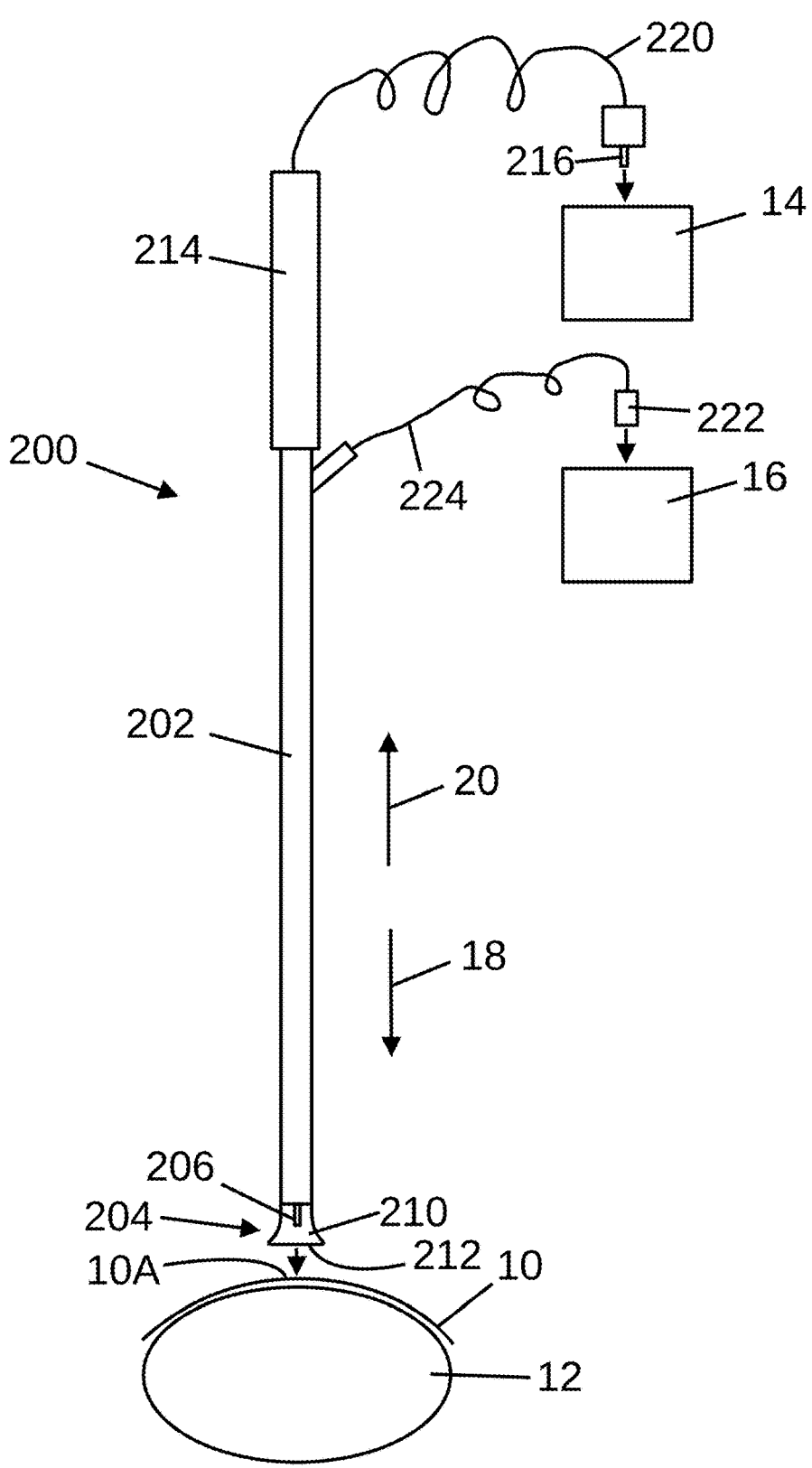
FIG. 5 is a simplified schematic view of an example monopolar electrosurgical pericardiotomy device.

FIG. 5 is a simplified schematic view of an example monopolar electrosurgical pericardiotomy device 200 according to at least some aspects of the present disclosure. The electrosurgical pericardiotomy device 200 may be used in connection with a pericardiotomy procedure including creating an opening through a patient's pericardium 10, such as to obtain access to the patient's heart 12. The pericardiotomy device 200 may be operatively coupled to an electrosurgical generator 14 and/or a vacuum source 16.

In the illustrated embodiment, the electrosurgical pericardiotomy device 200 includes an elongated shaft 202 and an end effector 204 disposed generally distally on the shaft 202. In some example embodiments, the shaft 202 may have an outer diameter of about 5.0 mm. The shaft 202 may be configured to be rigid, flexible, and/or malleable (e.g., plastically deformable), and the stiffness, flexibility, and/or malleability may vary over its proximal-distal length.

In the illustrated embodiment, the end effector 204 includes one or more electrodes 206 configured to be placed into contact with the target portion 10A of the pericardium 10. Energy from the electrosurgical generator 14 may be selectively supplied to the electrode 206 to cause the electrodes 206 to create an opening through the pericardium 10.

In the illustrated embodiment, the end effector 204 includes a tip portion 210. The electrode 206 may be disposed at least partially within the tip portion 210. The tip portion 210 may include an opening, such as a distal opening 212, configured to engage the pericardium 10 and allow the pericardium to contact the electrode 206. In some alternative embodiments, the opening may be oriented in another direction, such as generally laterally. In some example embodiments, the distal opening 212 may be generally circular. In some alternative embodiments, the opening may have another shape, such as a generally elongated channel. Vacuum from the vacuum source 16 may be selectively supplied to the tip portion 210, such as to separate and/or increase spacing between the target portion 10A of the pericardium from an external surface of the heart 12 and/or to draw the target portion 10A of the pericardium 10 into contact with the electrode 206. In some example embodiments, the tip portion 210 may be constructed from a substantially transparent material, which may facilitate visibility through the tip portion 210, such as visualization of the electrode 206. In other embodiments, at least a portion of the tip portion 210 may be constructed from a translucent material and/or an opaque material such as, without limitation, a radiopaque material.

In the illustrated embodiment, the electrosurgical pericardiotomy device 200 includes a handle 214 disposed proximally on the shaft 202. The handle 214 may be configured to allow a user to hold and manipulate the pericardiotomy device 200.

The pericardiotomy device 200 may include one or more electrical connectors 216, which may be used to electrically connect the electrosurgical pericardiotomy device 200 to the electrosurgical generator 14. In the illustrated embodiment, the electrical connector 216 is disposed on a cord 220 that includes one or more conductors and extends from the handle 214. For example, the electrical connector 216 may be in the form of a standard 3-pin monopolar connector. In other embodiments, the electrical connector 216 may be disposed on the handle 214 and may be configured to couple with an electrical cord 220 that attaches to the electrosurgical generator 14. (See, for example, FIG. 1.) In still further embodiments, the cord 220 and/or electrosurgical generator 14 may be incorporated into the handle 214 or permanently attached thereto.

The pericardiotomy device 200 may include at least one vacuum connector 222, which may be used to fluidically connect the pericardiotomy device 200 to the vacuum source 16. In the illustrated embodiment, a vacuum line 224 including one or more lumens extends from the shaft 202, and the vacuum connector 222 is disposed on the end of the line 224 that attaches to the vacuum source 16. In other embodiments, the vacuum connector 222 may be disposed generally proximally on the shaft 202 near the handle 214, and the vacuum connector 222 may be configured to couple with a vacuum line 224 extending from the vacuum source 16. (See, for example, FIG. 2.)

Figure 6:
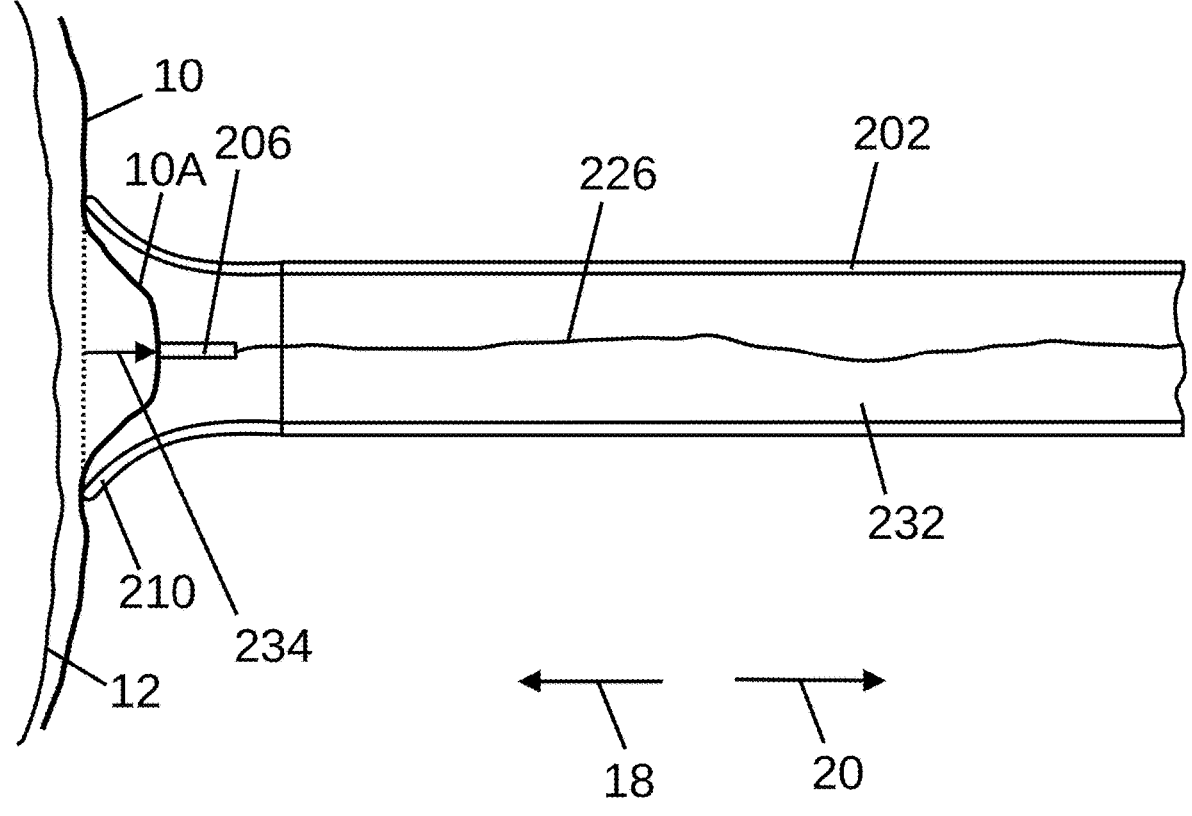
FIG. 6 is a simplified lateral section view of a distal portion of the electrosurgical pericardiotomy device of FIG. 5.
Figure 7:
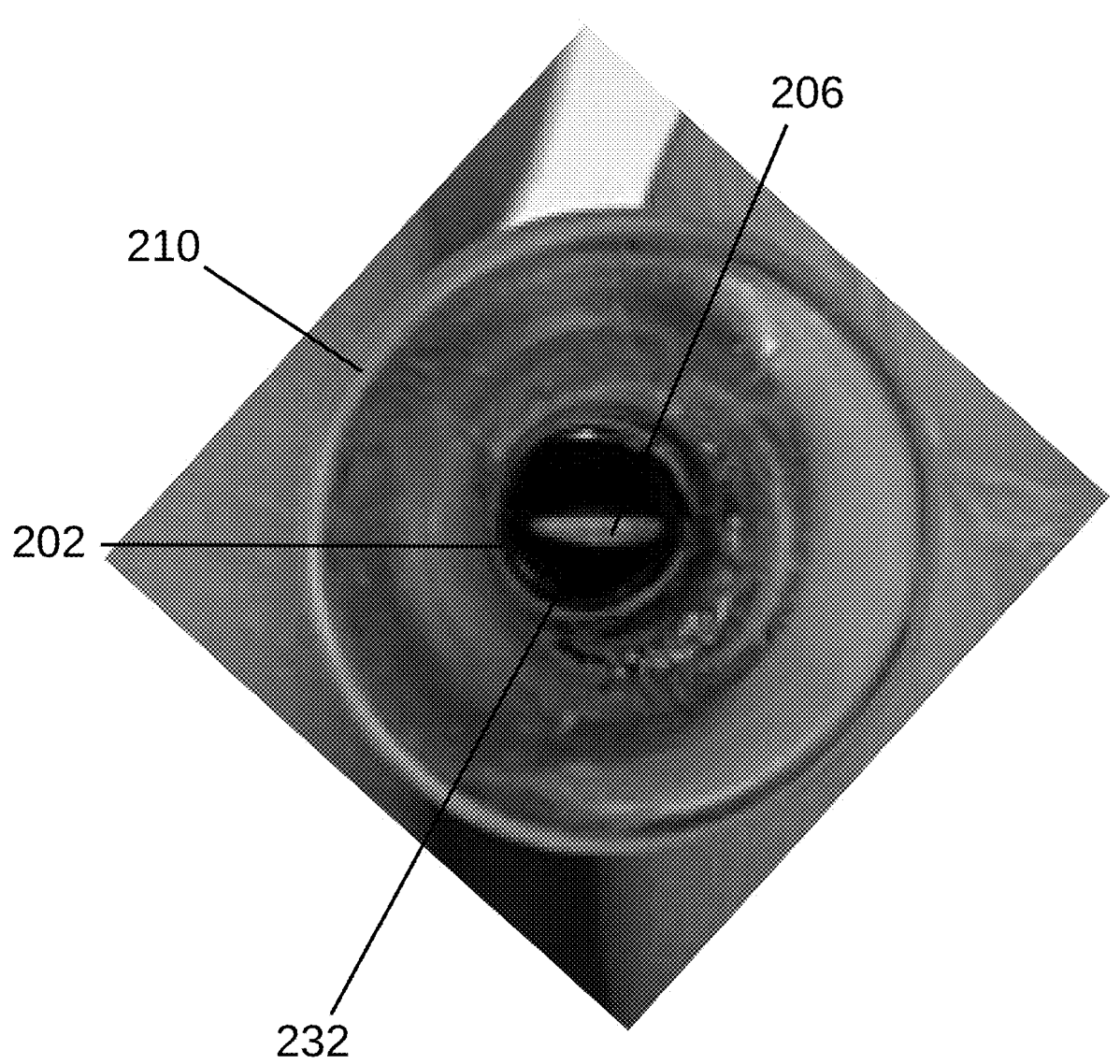
FIG. 7 is a detailed distal end view of the distal portion of the electrosurgical pericardiotomy device of FIG. 5.

FIG. 6 is a simplified lateral cutaway view of a distal portion of the electrosurgical pericardiotomy device 200 and FIG. 7 is a detailed distal end view of the distal portion of the electrosurgical pericardiotomy device 200, all according to at least some aspects of the present disclosure. Referring to FIG. 6, in the illustrated embodiment, the electrosurgical pericardiotomy device 200 includes one or more electrical conductors 226, which electrically connects the electrode 206 to the electrical connector 216 (FIG. 5). The electrical conductor 226 may extend proximally within the shaft 202 from proximate the electrode 206 to proximate the electrical connector 216. Referring to FIGS. 6 and 7, in the illustrated embodiment, the electrode 206 may be configured in the form of a single blade electrode. Specifically, the electrode 206 may be arranged generally diametrically with respect to the shaft 220. Referring to FIG. 6, in the illustrated embodiment, the electrode 206 is configured to direct electrical energy into the target portion 10A of the pericardium 10 in the vicinity of the electrode 206.

Referring to FIG. 6, in the illustrated embodiment, the electrode 206 is recessed proximally within the tip portion 210 at a distance shown by arrow 234. In other embodiments, the electrode 206 may be disposed at other proximal-distal positions within the tip portion 210, such as substantially even with the distal end of the tip portion 210 (e.g., zero distance recess). In yet other embodiments, the electrode 206 may be selectively repositionable in the distal 20 and proximal 18 directions to vary the proximal-distal positions within the tip portion 210.

Referring to FIG. 6, in the illustrated embodiment, at least a portion of the shaft 202 may at least partially define an internal channel 232. The channel 232 may be configured as a vacuum conduit fluidically interposing the tip portion 210 and the vacuum connector 222. Application of vacuum to the tip 210 (e.g., via the vacuum connector 222 and the internal channel 232) may be operative to draw the target portion 10A of the pericardium 10 into the tip portion 210 as illustrated by arrow 234. In this embodiment, drawing the target portion 10A of the pericardium 10 into the tip portion 210 by application of vacuum pulls the pericardium 10 into contact with the electrode 206. In the illustrated embodiment, because the electrode 206 is recessed proximally within the tip portion 210, drawing the pericardium 10 into the tip portion 210 by application of vacuum also creates and/or increases the distance between the surface of the heart 12 and the location where electrical energy is applied to the pericardium 10 by the electrode 206. Thus, the likelihood of injury to the heart 12 (e.g., due to energy delivered by the electrode 206) may be reduced.

Referring to FIG. 6, in the illustrated embodiment, the tip portion 210 may be formed in a wide bell shape, similar to that described above with reference to FIG. 2.

Figure 8:
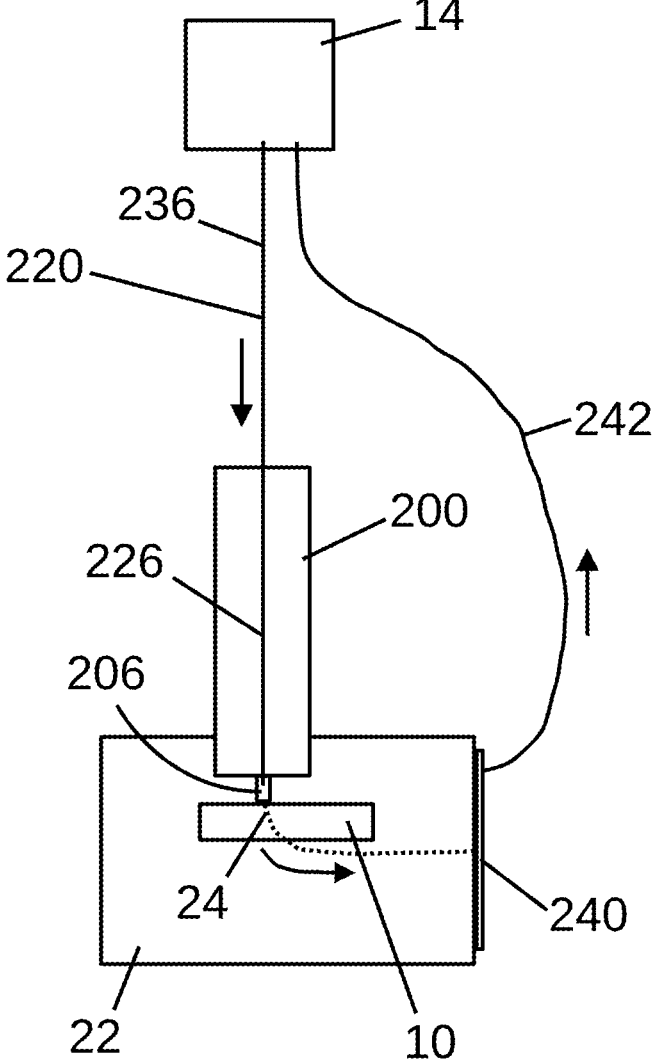
FIG. 8 is a simplified block diagram illustrating example monopolar operation of the electrosurgical pericardiotomy device of FIG. 5.

FIG. 8 is a simplified block diagram illustrating example monopolar operation of the electrosurgical pericardiotomy device 200, according to at least some aspects of the present disclosure. As used herein, "monopolar" may refer to an electrosurgical device configuration in which an active electrode is disposed substantially at a surgical site and a return electrode is disposed elsewhere on the patient's body, away from the surgical site, and in electrical contact with the patient's body. It will be understood that the electrosurgical generator 14 may supply direct current and/or alternating current of any suitable magnitude at any suitable voltage and in any suitable waveform (e.g., square wave, sine wave, etc.). However, for clarity, FIG. 8 illustrates current flow in one direction. It will be understood that other embodiments described herein as having a monopolar configuration may be arranged and operated in a generally similar manner.

Referring to FIG. 8, electrical energy flow from the electrosurgical generator 14, through an electrically conductive line 236 forming the cord 220 to the pericardiotomy device 200. In particular, the electrical energy flows through the electrical conductor 226 to the first electrode 206 (e.g., acting as the active electrode). From the electrode 206, the electrical energy flows through the target tissue (e.g., the pericardium 10) to a second electrode 240 (e.g., acting as the return electrode). Generally, the electrosurgical effect of the electrical energy is directed at the target tissue (e.g., the pericardium 10) and has minimal or no effects on other portions of the patient's body 22. From the second (return) electrode 240, the electrical energy flows through an electrically conductive line 242 to the electrosurgical generator 14. In the illustrated monopolar configuration, the electro surgical effect of the electrodes 206 is applied substantially in the vicinity of the location 24 where the electrical energy is directed at the target tissue (e.g., at the surgical site). The electrical energy ablates the target tissue at the surgical site, thereby creating an opening through the pericardium. In one example embodiment, the electrode 206 may be about 2.3 mm long, and the resulting opening may be about 2.3 mm long. The opening may be generally oval or generally circular in shape, for example. If a larger opening is desired, the electrode 206 may be repositioned and reactivated to create a larger opening. Alternatively, the opening may be expanded using surgical instruments, such as by using a grasper to pull the pericardium away from the heart and expanding the opening with scissors or electrocautery.

FIGS. 9-15 illustrate various alternative example tip portion and electrode configurations. It will be understood that these and other configurations may be used in connection with various electrosurgical pericardiotomy devices according to at least some aspects of the present disclosure.

Figure 9:
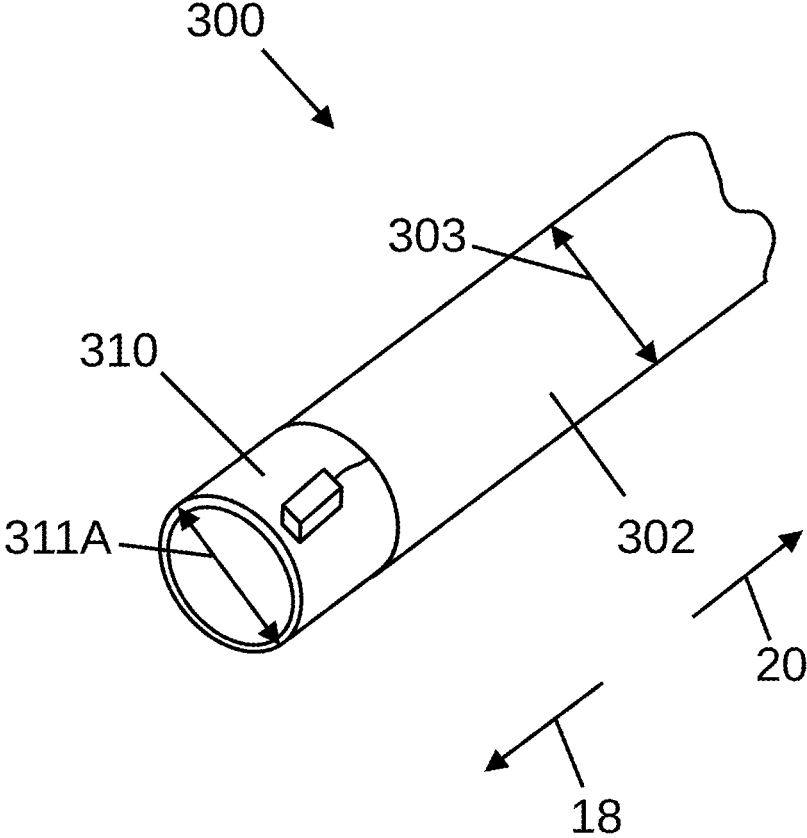
FIG. 9 is a simplified perspective view of the distal portion of an alternative example electrosurgical pericardiotomy device including a tip portion generally in the form of a right circular cylinder.

FIG. 9 is a simplified perspective view of the distal portion of an alternative example electrosurgical pericardiotomy device 300, according to at least some aspects of the present disclosure. The pericardiotomy device 300 is generally similar in construction and operation to the pericardiotomy devices described elsewhere herein, and repeated description of similar elements is omitted for brevity. In the illustrated embodiment, the shape of the tip portion 310 of the electrosurgical pericardiotomy device 300 differs from the shapes of the tip portions 110, 210 of the previously described pericardiotomy devices 100, 200. In this embodiment, the tip portion 310 is generally in the form of a right circular cylinder having a substantially constant outer diameter 311A. The outer diameter 311A of the tip portion 310 may be substantially the same as the outer diameter 303 of the shaft 302. In some example embodiments, the tip portion 310 may be integrally and/or monolithically formed with the shaft 302. In some such embodiments, the tip portion 310 may be constructed from the same material as the shaft 302.

Figure 10:
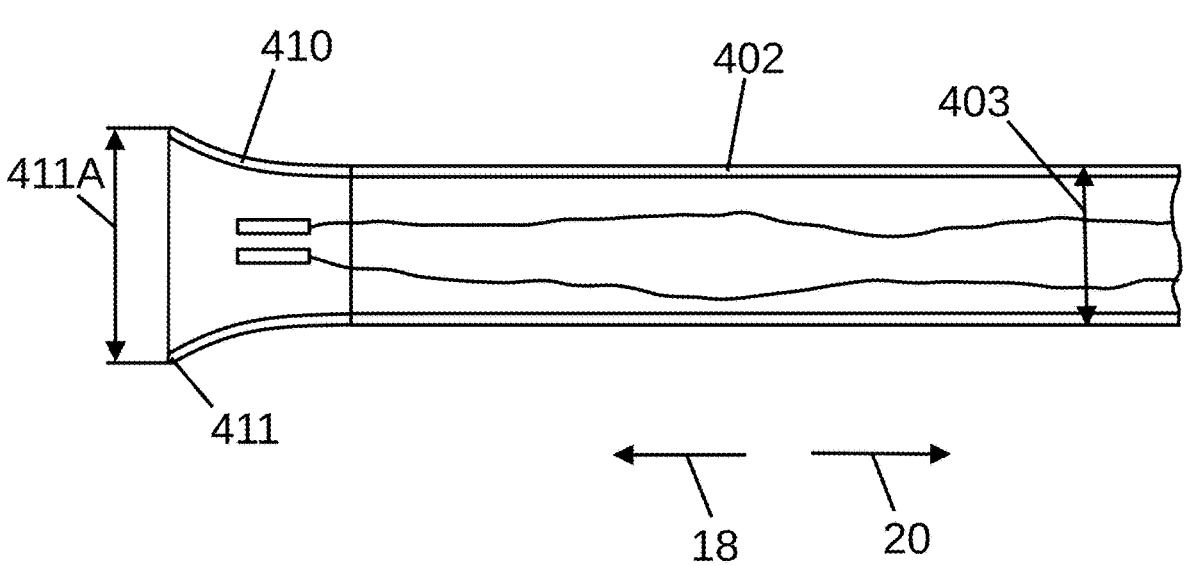
FIG. 10 is a simplified lateral cutaway view of the distal portion of an alternative example electrosurgical pericardiotomy device including a tip portion generally in the form of a narrow bell shape.

FIG. 10 is a simplified lateral cutaway view of the distal portion of an alternative example electrosurgical pericardiotomy device 400, according to at least some aspects of the present disclosure. The electrosurgical pericardiotomy device 400 is generally similar in construction and operation to the pericardiotomy devices described elsewhere herein, and repeated description of similar elements is omitted for brevity. In the illustrated embodiment, the shape of the tip portion 410 of the pericardiotomy device differs from the shapes of the tip portions 110, 210, 310 of the previously described pericardiotomy devices 100, 200, 300. In this embodiment, the tip portion 410 is generally in the form of a narrow bell shape. For example, the proximal end of the tip portion 410 may have an outer diameter approximately the same as the outer diameter 403 of the shaft 402 (e.g., about 5.0 mm). The distal end 411 of the tip portion 410 may have an outer diameter 411A that is greater than the outer diameter 403 of the shaft 402. In some embodiments, the radially outer surface of the tip portion 410 may continuously curve, such as in a generally concave manner, between the proximal portion of the tip portion 410 near the shaft 402 and the distal end 411 of the tip portion 410. For example, the maximum outer diameter 411A of the tip portion 410 (e.g., proximate the distal end) may be about 8 mm. Thus, the maximum outer diameter 411A of the tip portion 410 may be about 1.6 times the maximum shaft 402 diameter 403.

Figure 11:
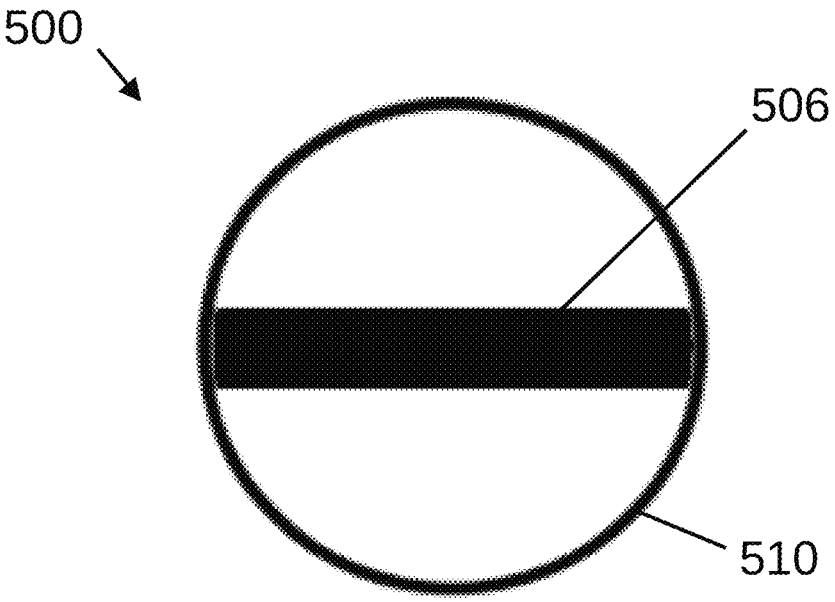
FIG. 11 is a simplified distal end view of an alternative example electrosurgical pericardiotomy device including an electrode in the form of a generally rectangular bar.

FIG. 11 is a simplified distal end view of an alternative example electrosurgical pericardiotomy device 500, according to at least some aspects of the present disclosure. The pericardiotomy device 500 is generally similar in construction and operation to the pericardiotomy devices elsewhere herein, and repeated description of similar elements is omitted for brevity. In the illustrated embodiment, the shape of the electrode 506 differs from the shapes of the electrodes of the previously described pericardiotomy devices. In this embodiment, the electrode 506 is generally in the form of a generally rectangular bar, which is disposed generally diametrically within the tip portion 510. Although the illustrated embodiment is configured for monopolar operation, alternative embodiments may be configured for bipolar operation.

Figure 12:
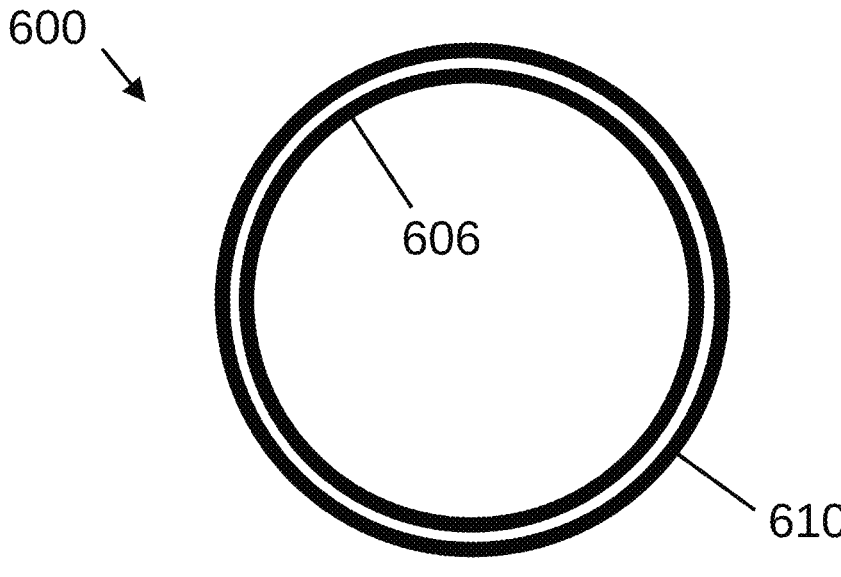
FIG. 12 is a simplified distal end view of an alternative example electrosurgical pericardiotomy device including an electrode in the form of a generally circular ring.

FIG. 12 is a simplified distal end view of an alternative example electrosurgical pericardiotomy device 600, according to at least some aspects of the present disclosure. The pericardiotomy device 600 is generally similar in construction and operation to the pericardiotomy devices elsewhere herein, and repeated description of similar elements is omitted for brevity. In the illustrated embodiment, the shape of the electrode 606 differs from the shapes of the electrodes of the previously described pericardiotomy devices. In this embodiment, the electrode 606 is generally in the form of a generally circular ring, which is generally centrally disposed within the tip portion 610. Although the illustrated embodiment is configured for monopolar operation, alternative embodiments may be configured for bipolar operation.

Figure 13:
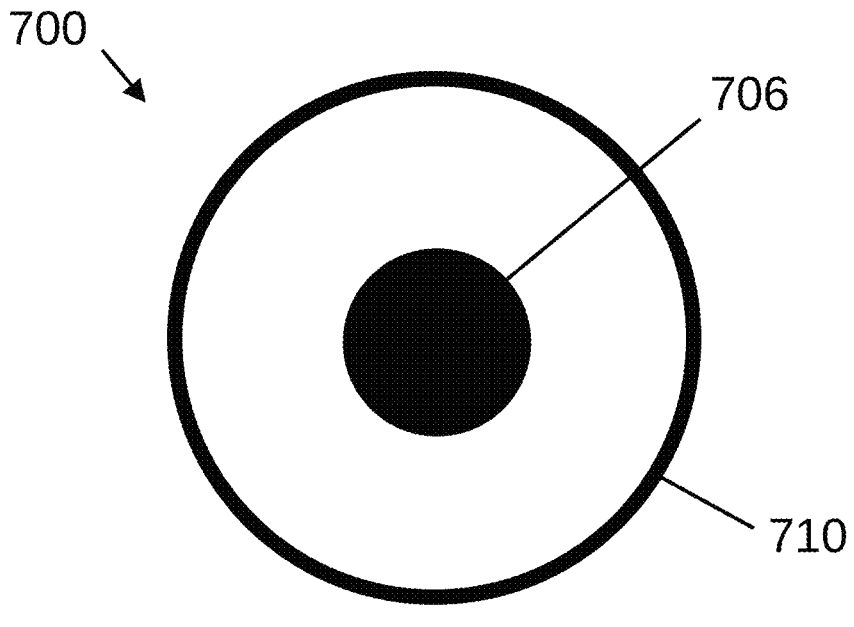
FIG. 13 is a simplified distal end view of an alternative example electrosurgical pericardiotomy device including an electrode in the form of a generally circular dot.

FIG. 13 is a simplified distal end view of an alternative example electrosurgical pericardiotomy device 700, according to at least some aspects of the present disclosure. The pericardiotomy device 700 is generally similar in construction and operation to the pericardiotomy devices elsewhere herein, and repeated description of similar elements is omitted for brevity. In the illustrated embodiment, the shape of the electrode 706 differs from the shapes of the electrodes of the previously described pericardiotomy devices. In this embodiment, the electrode 706 is generally in the form of a generally circular dot, which is disposed generally centrally within the tip portion 710. Although the illustrated embodiment is configured for monopolar operation, alternative embodiments may be configured for bipolar operation.

Figure 14:
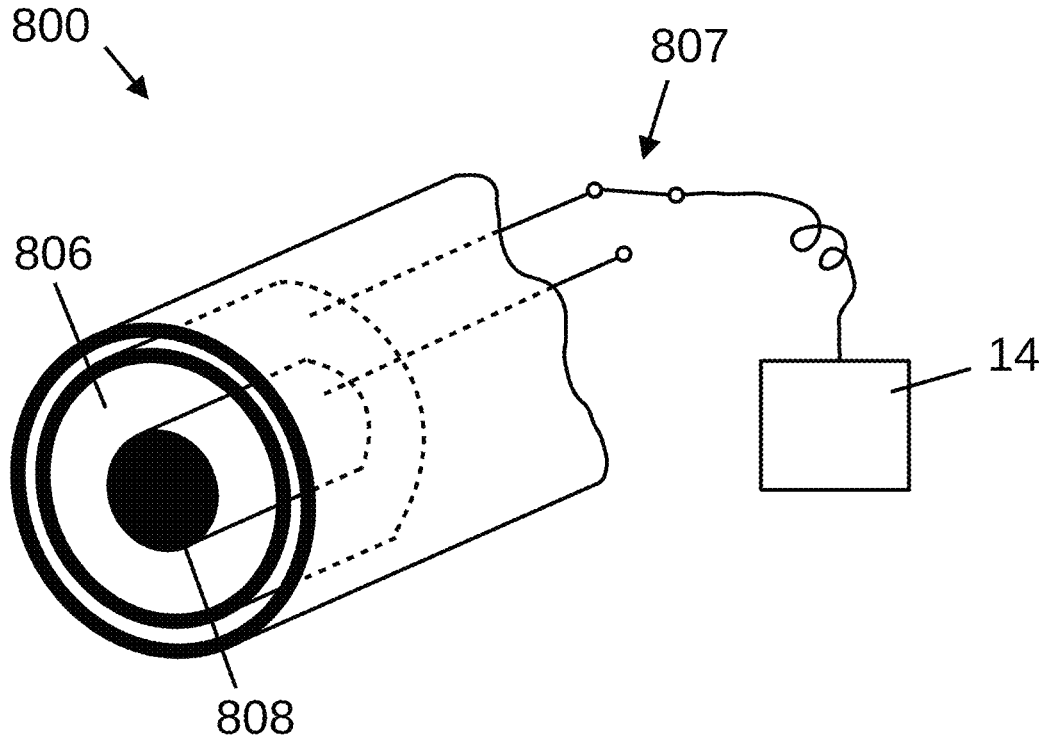
FIG. 14 is a simplified distal end view of an alternative example electrosurgical pericardiotomy device including a first electrode in the form of a generally circular ring and a second electrode in the form of a generally circular dot.

FIG. 14 is a simplified distal end view of an alternative example electrosurgical pericardiotomy device 800, according to at least some aspects of the present disclosure. The pericardiotomy device 800 is generally similar in construction and operation to the pericardiotomy devices elsewhere herein, and repeated description of similar elements is omitted for brevity. In the illustrated embodiment, the configuration of the electrodes 806, 808 differs from the configurations of the electrodes of the previously described pericardiotomy devices. In this embodiment, a first electrode 806 is generally in the form of a generally circular ring positioned centrally within the tip portion 810. A second electrode 808 is generally in the form of a generally circular dot positioned centrally within the ring of the first electrode 806. Additionally, the illustrated embodiment includes a switch 807, which is configured to selectively connect one of the first electrode 806 and the second electrode 808 to the electrosurgical generator 14 for monopolar operation utilizing the selected electrode 806, 808. Although the illustrated embodiment is configured for monopolar operation using the selected electrode 806, 808 while the other electrode 806, 808 remains inactive, alternative embodiments may be configured for bipolar operation, such as simultaneously utilizing both electrodes 806, 808.

Figure 15:
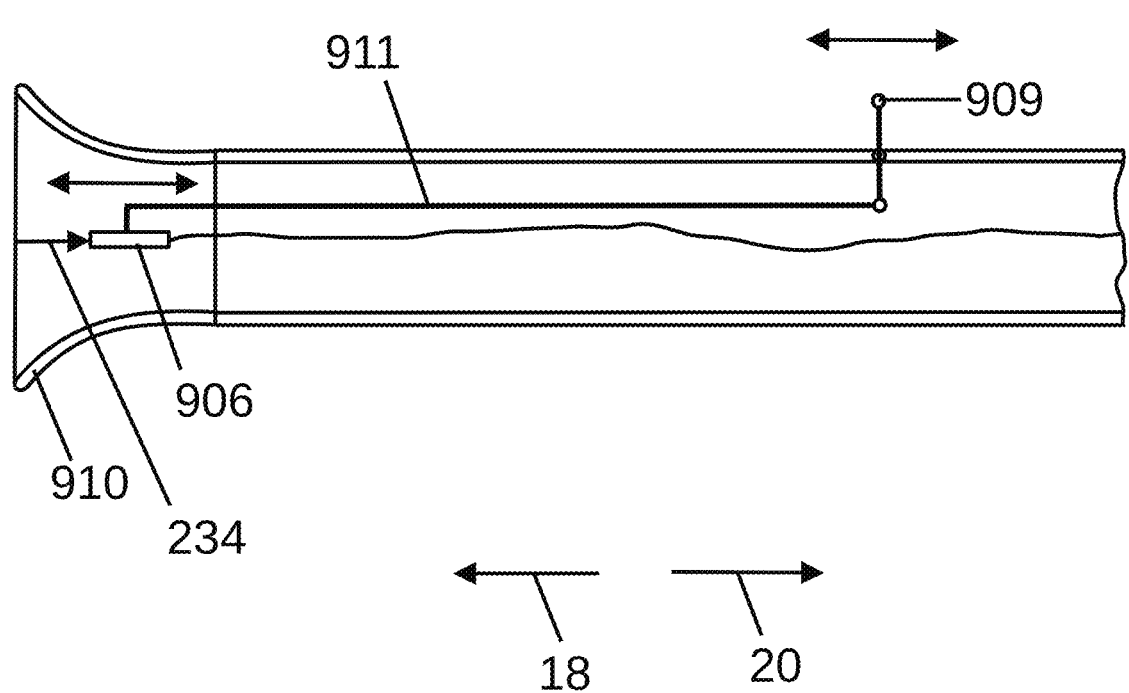
FIG. 15 is a simplified lateral cutaway view of a distal portion of an alternative example electrosurgical pericardiotomy device including a repositionable electrode.

FIG. 15 is a simplified lateral cutaway view of a distal portion of an alternative example electrosurgical pericardiotomy device 900, according to at least some aspects of the present disclosure. The pericardiotomy device 900 is generally similar in construction and operation to the pericardiotomy devices elsewhere herein, and repeated description of similar elements is omitted for brevity. In the illustrated embodiment, the electrode 906 is repositionable. For example, the electrode 906 may be movable proximally 20 and/or distally 18 relative to the tip portion 910, such as using an actuator 909 coupled to the electrode 906 by a linkage 911. Accordingly, the distance at which the electrode 906 is recessed proximally within the tip portion 910 (shown by arrow 234) is adjustable. Although the illustrated embodiment is configured for monopolar operation, alternative embodiments may be configured for bipolar operation, which may include, for example, a pair of bipolar electrodes in which at least one of the electrodes is repositionable.

Figure 16:
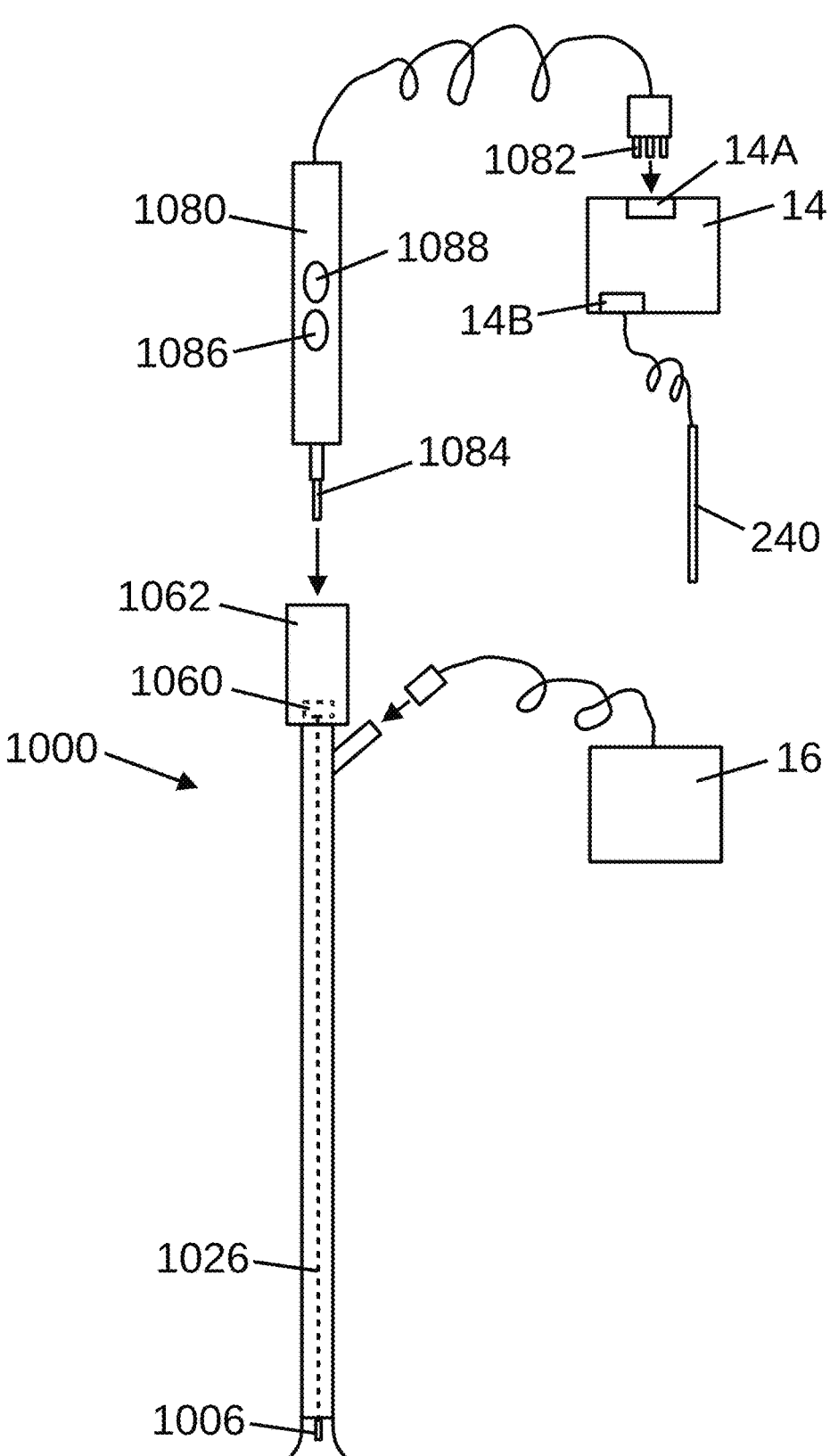
FIG. 16 is a simplified schematic view of an example monopolar electrosurgical pericardiotomy device configured for use with off-the-shelf electrosurgical devices.
Figure 17:
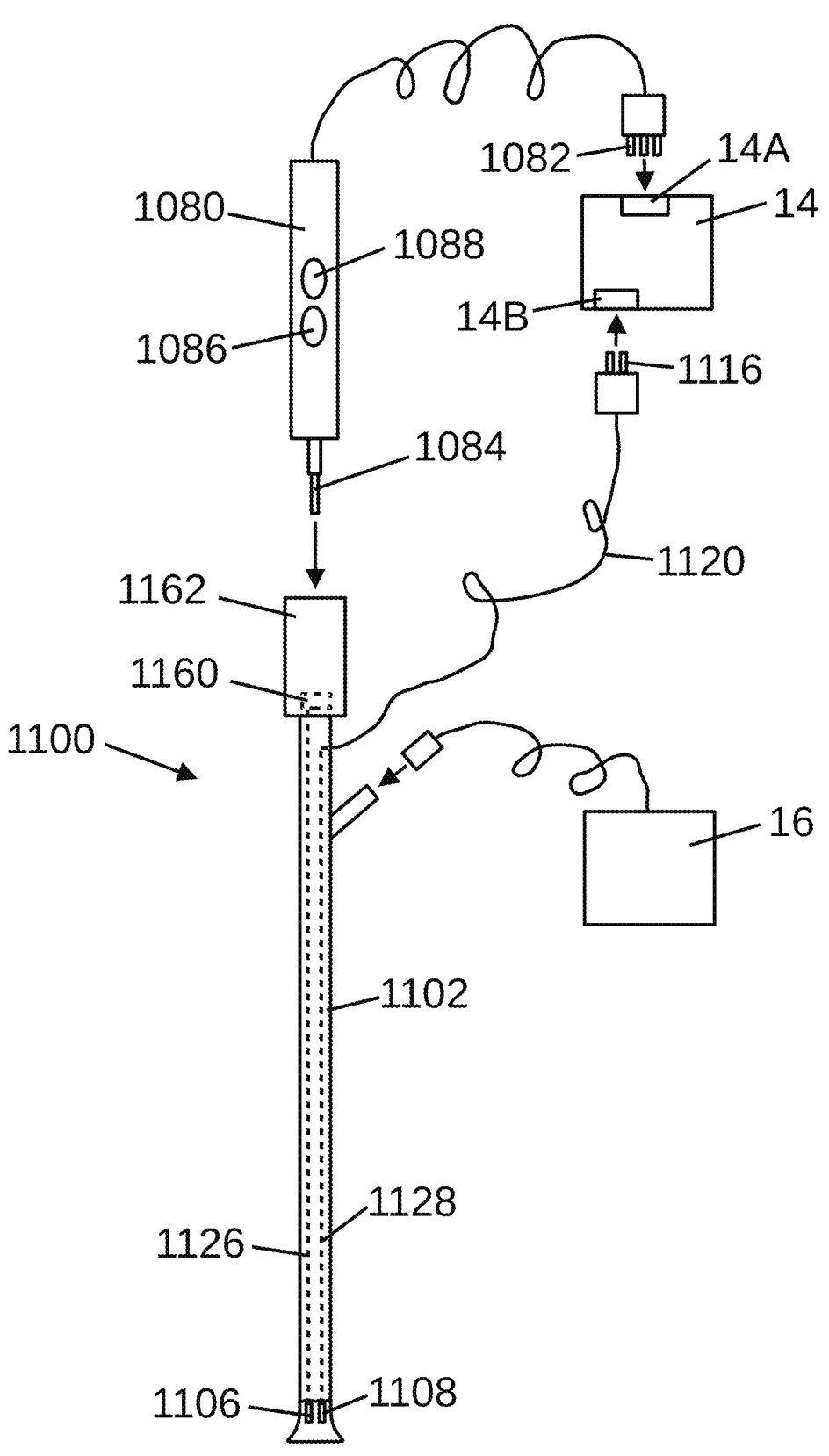
FIG. 17 is a simplified schematic view of an example bipolar electrosurgical pericardiotomy device configured for use with off-the-shelf electrosurgical devices.

FIGS. 16 and 17 illustrate alternative example electrosurgical pericardiotomy devices that are configured for use with off-the-shelf electrosurgical devices. It will be understood that except where explicitly stated otherwise, these embodiments may be constructed and operated similar to the embodiments described above, and repeated description is omitted for brevity.

FIG. 16 is a simplified schematic view of an example monopolar electrosurgical pericardiotomy device 1000, according to at least some aspects of the present disclosure. Generally, the electrosurgical pericardiotomy device 1000 may be similar to the pericardiotomy device 200 described above with reference to FIGS. 5-8. The pericardiotomy device 1000 differs from the pericardiotomy device 200 in that the pericardiotomy device 1000 is configured for use in connection with an off-the-shelf electrosurgical device 1080. Generally, in this embodiment, the off-the-shelf electrosurgical device 1080 is configured for monopolar operation.

The present disclosure contemplates that various off-the-shelf electrosurgical devices 1080 are commonly utilized in surgical procedures. Such off-the-shelf electrosurgical devices 1080 may be generally familiar and may be readily available in operating rooms and/or may be used in a wide variety of surgical procedures. Such off-the-shelf electrosurgical devices 1080 may not, however, be specifically configured for use in connection with pericardiotomy procedures. The off-the-shelf electrosurgical device 1080 may include, for example, a Bovie® electrosurgical pencil available from Symmetry Surgical Inc. of Nashville, Tennessee. Generally, in the illustrated embodiment, the off-the-shelf electrosurgical device 1080 includes an electrosurgical generator connector 1082 (e.g., a standard 3-pin monopolar connector), configured to electrically connect to a monopolar connection 14A of the electrosurgical generator 14, and an active electrode 1084. Electrical energy may be delivered to the active electrode 1084 upon activation of an actuator, such as one or more buttons 1086, 1088. For example, a first button 1086 may cause delivery of electrical energy to the active electrode in a "cut" mode, and a second button 1088 may cause delivery of electrical energy to the active electrode in a "coagulate" mode. Alternative embodiments my utilize foot pedals or other user interface devices as actuators to control operation of the off-the-shelf electrosurgical device 1080.

In the illustrated embodiment, the pericardiotomy device 1000 is configured to operatively couple to the off-the-shelf electrosurgical device 1080. Specifically, in this embodiment, the pericardiotomy device 1000 includes an off-the-shelf electrosurgical device electrical connector 1060 configured to electrically connect with the active electrode 1084 of the off-the-shelf electrosurgical device 1080. The off-the-shelf electrosurgical device electrical connector 1060 is electrically coupled to the electrode 1006 of the pericardiotomy device 1000, such as by one or more electrical conductors 1026. In some example embodiments, the pericardiotomy device 1000 may include an off-the-shelf electrosurgical device mechanical connector 1062 configured to mechanically couple the off-the-shelf electrosurgical device 1080 and the pericardiotomy device 1000. In the illustrated embodiment, the off-the-shelf electrosurgical device mechanical connector 1062 is arranged to receive a portion of the off-the-shelf electrosurgical device 1080 therein, including the active electrode 1084. When coupled together, the active electrode 1084 is not exposed externally and the buttons 1086, 1088 remain exposed and operable by a user.

In use, the off-the-shelf electrosurgical device 1080 is coupled to the pericardiotomy device 1000, and the off-the-shelf electrosurgical device 1080 is connected to the electrosurgical generator 14. When one of the buttons 1086, 1088 is depressed (e.g., thereby activating the off-the-shelf electrosurgical device 1080), electrical energy from the electrosurgical generator 14 is delivered to the electrode 1006 of the pericardiotomy device 1000 via the off-the-shelf electrosurgical device 1080. A return electrode 240, located elsewhere on the patient's body, away from the surgical site, and connected to a return electrode connection 14B of the electrosurgical generator completes the electrical path.

Although the monopolar pericardiotomy device 1000 is configured for monopolar operation in connection with a monopolar off-the-shelf electrosurgical device 1080, it will be understood that a generally similar configuration may be utilized in a bipolar pericardiotomy device configured for bipolar operation in connection with a bipolar off-the-shelf electrosurgical device. Such a device may be generally similar to the bipolar pericardiotomy device 100 described above with reference to FIGS. 1-4 and may include two electrodes electrically coupled to respective electrodes of the bipolar off-the-shelf electrosurgical device.

FIG. 17 is a simplified schematic view of an example bipolar electrosurgical pericardiotomy device 1100, according to at least some aspects of the present disclosure. Generally, the pericardiotomy device 1100 may be similar to the bipolar pericardiotomy device 100 (described above with reference to FIGS. 1-4) and the monopolar pericardiotomy device 1000 (described above with reference to FIG. 16). As with the monopolar pericardiotomy device 1000, the bipolar pericardiotomy device 1100 is configured for use in connection with a monopolar off-the-shelf electrosurgical device 1080. The bipolar pericardiotomy device 1100 differs from the monopolar pericardiotomy device 1000 in that the bipolar pericardiotomy device 1100 is configured for bipolar operation generally similar to the bipolar pericardiotomy device 100. In particular, both electrodes 1106, 1108 are located on the pericardiotomy device 1100 for use substantially at the surgical site. In the illustrated embodiment, the bipolar pericardiotomy device 1100 uses electrical energy supplied via the monopolar off-the-shelf electrosurgical device 1080 described above in connection with the monopolar pericardiotomy device 1000.

In the illustrated embodiment, the bipolar pericardiotomy device 1100 is configured to operatively couple to the off-the-shelf electrosurgical device 1080. The pericardiotomy device 1100 includes an off-the-shelf electrosurgical device electrical connector 1160 configured to electrically connect with the active electrode 1084 of the off-the-shelf electrosurgical device 1080. The off-the-shelf electrosurgical device electrical connector 1160 is electrically coupled to a first electrode 1106 of the pericardiotomy device 1100, such as by one or more electrical conductors 1126. In some example embodiments, the pericardiotomy device 1100 may include an off-the-shelf electrosurgical device mechanical connector 1162 configured to mechanically couple the off-the-shelf electrosurgical device 1080 and the pericardiotomy device 1100. In the illustrated embodiment, the off-the-shelf electrosurgical device mechanical connector 1162 is arranged to receive a portion of the off-the-shelf electrosurgical device 1080 therein, including the active electrode 1084. When coupled together, the active electrode 1084 is not exposed externally and the buttons 1086, 1088 remain exposed and operable by a user.

In the illustrated embodiment, the bipolar pericardiotomy device 1100 also includes one or more electrical connectors 1116, which may be used to electrically connect the bipolar pericardiotomy device 1100 to the electrosurgical generator 14. In this embodiment, the electrical connector 1116 is disposed on a cord 1120 that includes one or more conductors and extends from the shaft 1102. The electrical connector 1116 is electrically coupled to the second electrode 1108 by one or more electrical conductors 1128. In other embodiments, the electrical connector 1116 may be disposed on the shaft 1102 and may be configured to couple with an electrical cord 1120 that attaches to the electrosurgical generator 14. (See, for example, FIG. 1.)

In use, in the illustrated embodiment, the off-the-shelf electrosurgical device 1080 is coupled to the bipolar pericardiotomy device 1100, and the off-the-shelf electrosurgical device 1080 is connected to the electrosurgical generator 14. Specifically, the electrosurgical generator connector 1082 of the off-the-shelf electrosurgical device 1080 is connected to the monopolar connection 14A on the electrosurgical generator 14, the same as it would be for normal use of the off-the-shelf electrosurgical device 1080 separate from the pericardiotomy device 1100. Also, the electrical connector 1116 of the pericardiotomy device 1100 is configured to be connected to the return electrode connection 14B of the electro surgical generator 14. That is, the return electrode connection 14B of the electrosurgical generator 14 is connected to the electrical connector 1116 of the pericardiotomy device 1100, rather than being connected to the return electrode 240 (FIG. 8) as it would normally be in a monopolar operation configuration. Accordingly, from the perspective of the electrosurgical generator 14 and the off-the-shelf electrosurgical device 1080, the off-the-shelf electrosurgical device 1080 is connected for normal monopolar operation. However, both the active electrode connection 14A and return electrode connection 14B couple to respective electrodes 1106, 1108 of the pericardiotomy device 1100 arranged for use at the surgical site, and the pericardiotomy device 1100 is configured for bipolar operation.

When one of the buttons 1086, 1088 is depressed, electrical energy from the electrosurgical generator 14 is delivered to the first electrode 1106 of the bipolar pericardiotomy device 1100 via the monopolar connection 14A and the off-the-shelf electrosurgical device 1080. The second electrode 1108 of the pericardiotomy device 1100, also located at the surgical site, completes the electrical path to the electrosurgical generator 14 via the cord 1120 and the electrosurgical generator's 14 return electrode connection 14B.

Figure 18:
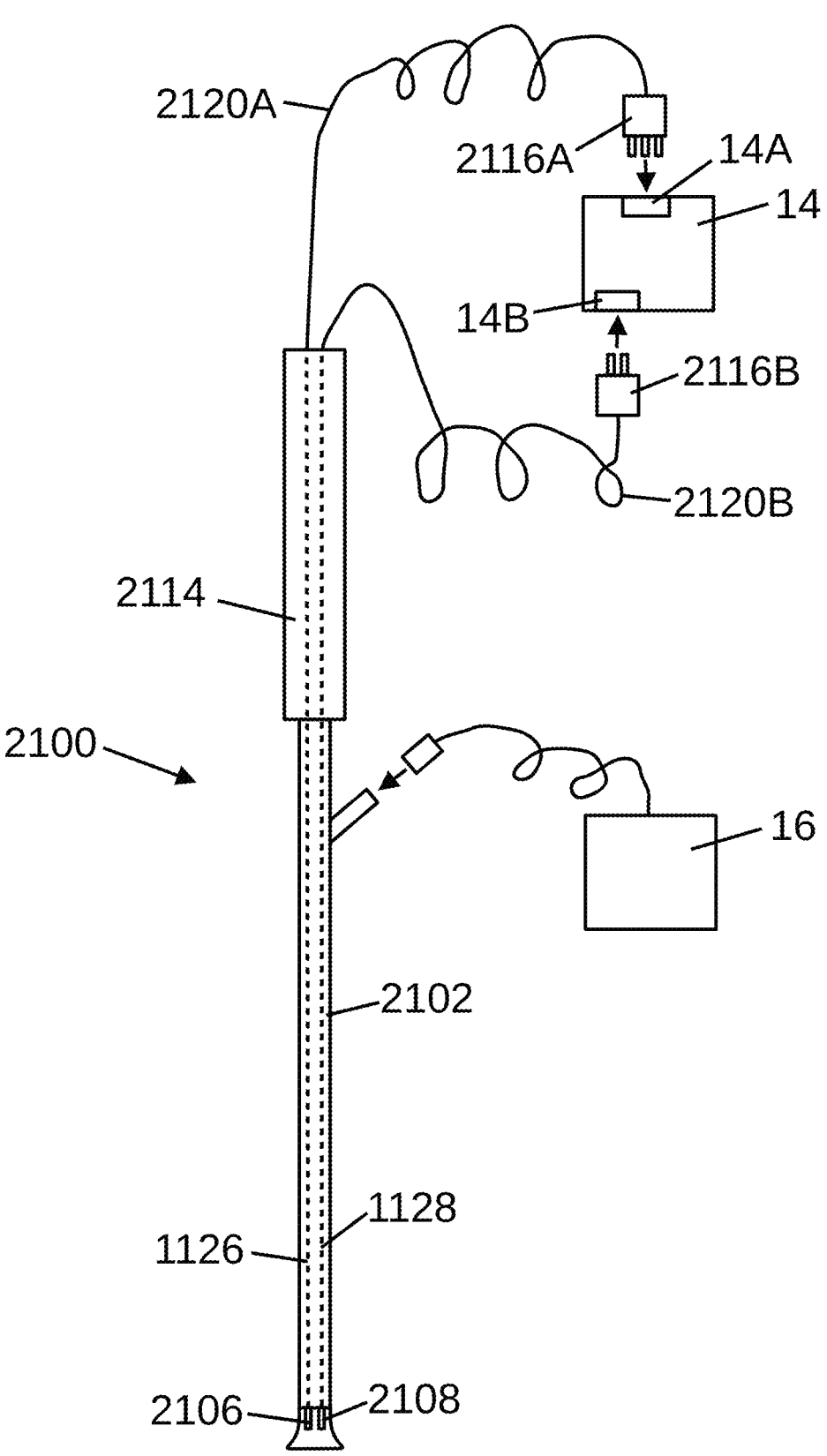
FIG. 18 is a simplified schematic view of an alternative example bipolar electrosurgical pericardiotomy device; all in accordance with at least some aspects of the present disclosure.

FIG. 18 is a simplified schematic view of an alternative example bipolar electrosurgical pericardiotomy device 2100, according to at least some aspects of the present disclosure. The pericardiotomy device 2100 is generally similar in construction and operation to the pericardiotomy devices elsewhere herein, and repeated description of similar elements is omitted for brevity. In particular, the pericardiotomy device 2100 may be similar to the bipolar electrosurgical pericardiotomy device 100 (described above with reference to FIGS. 1-4) and the bipolar electrosurgical pericardiotomy device 1100 (described above with reference to FIG. 17). As with the bipolar electrosurgical pericardiotomy device 1100 of FIG. 17, the pericardiotomy device 2100 is configured to use the monopolar connection 14A and return electrode connection 14B of the electrosurgical generator 14. Unlike the pericardiotomy device 1100, however, the pericardiotomy device 2100 is not configured for use in connection with an off-the-shelf electrosurgical device 1080 between the pericardiotomy device 2100 and the electrosurgical generator 14. Instead, the pericardiotomy device 2100 may be configured to connect directly to the electrosurgical generator 14.

Referring to FIG. 18, in the illustrated embodiment, electrodes 2106, 2108 are located on the pericardiotomy device 2100 for bipolar operation substantially at the surgical site. The pericardiotomy device 2100 includes one or more electrical connectors 2116A, 2116B, which may be used to electrically connect the bipolar pericardiotomy device 2100 to the electrosurgical generator 14. In this embodiment, the electrical connectors 2116A, 2116B are disposed on one or more cords 2120A, 2120B that include one or more conductors and extend from a handle 2114, which is proximally disposed on a shaft 2102. In other embodiments, one or more of the electrical connectors 2116A, 2116B may be disposed on the handle 2114 and/or shaft 2102 and may be configured to couple with one or more electrical cords 2120A, 2120B extending from the electrosurgical generator 14. (See, for example, FIG. 1.)

In use, in the illustrated embodiment, the bipolar pericardiotomy device 2100 is directly connected to the electrosurgical generator 14 (e.g., without an interposed off-the-shelf electrosurgical device 1080 (FIG. 17)). Specifically, one electrical connector 2116A is connected to the monopolar connection 14A on the electrosurgical generator 14. Also, the other electrical connector 2116B of the pericardiotomy device 2100 is connected to the return electrode connection 14B of the electrosurgical generator 14. Accordingly, from the perspective of the electrosurgical generator 14, the electrosurgical pericardiotomy device 2100 is connected like a monopolar off-the-shelf electrosurgical device. However, both the active electrode connection 14A and return electrode connection 14B couple to respective electrodes 2106, 2108 of the pericardiotomy device 2100, which are arranged for use at the surgical site, and the pericardiotomy device 2100 is configured for bipolar operation.

The present disclosure contemplates that some electrosurgical generators 14 may be configured to deliver more power in monopolar modes of operation than in bipolar modes of operation. Accordingly, in some circumstances, the bipolar pericardiotomy devices 1100, 2100 (using the monopolar output of the electrosurgical generator 14) may be capable of delivering greater electrosurgical energy than a bipolar pericardiotomy device using a conventional bipolar output of an electrosurgical generator 14.

Example methods of using electrosurgical pericardiotomy devices 100, 200, 300, 400, 500, 600, 700, 800, 900, 1000, 1100, 2100 according to at least some aspects of the present disclosure may include one or more of the following operations, in any combination. An opening 112, 212 of a tip portion 110, 210, 310, 410, 510, 610, 710, 910 of an end effector 104, 204 of an electrosurgical pericardiotomy device 100, 200, 300, 400, 500, 600, 700, 800, 900, 1000, 1100, 2100 may be engaged with a pericardium 10. The end effector 104, 204 may include the tip portion 110, 210, 310, 410, 510, 610, 710, 910 and an electrosurgical electrode 106, 108, 206, 506, 606, 706, 806, 808, 906, 1006, 1106, 1108, 2106, 2108 disposed proximate the tip portion 110, 210, 310, 410, 510, 610, 710, 910. A target portion 10A of the pericardium 10 may be separated or further separated from a heart 12 by applying vacuum to the tip portion 110, 210, 310, 410, 510, 610, 710, 910. The electrosurgical electrode 106, 108, 206, 506, 606, 706, 806, 808, 906, 1006, 1106, 1108, 2106, 2108 may be contacted with the target portion 10A of the pericardium 10. An opening may be created through the target portion 10A of the pericardium 10 by applying electrosurgical energy to the at least one electrosurgical electrode 106, 108, 206, 506, 606, 706, 806, 808, 906, 1006, 1106, 1108, 2106, 2108.

In some embodiments, the electrosurgical electrode 106, 108, 206, 506, 606, 706, 806, 808, 906, 1006, 1106, 1108, 2106, 2108 may be recessed within the tip portion 110, 210, 310, 410, 510, 610, 710, 910, and contacting the electrosurgical electrode 106, 108, 206, 506, 606, 706, 806, 808, 906, 1006, 1106, 1108, 2106, 2108 of the electrosurgical pericardiotomy device 100, 200, 300, 400, 500, 600, 700, 800, 900, 1000, 1100, 2100 disposed proximate the tip portion 110, 210, 310, 410, 510, 610, 710, 910 with the target portion 10A of the pericardium 10 may include drawing the target portion 10A of the pericardium 10 into the tip portion 110, 210, 310, 410, 510, 610, 710, 910. In some embodiments, the opening 112, 212 may include a distal opening 112, 212, and the electrosurgical electrode 106, 108, 206, 506, 606, 706, 806, 808, 906, 1006, 1106, 1108, 2106, 2108 may be recessed proximally within the tip portion 110, 210, 310, 410, 510, 610, 710, 910 relative to the distal opening 112, 212. Drawing the target portion 10A of the pericardium 10 into the tip portion 110, 210, 310, 410, 510, 610, 710, 910 may include drawing the target portion 10A of the pericardium 10 proximally into the tip portion 110, 210, 310, 410, 510, 610, 710, 910.

In some embodiments, before engaging the opening 112, 212 of the tip portion 110, 210, 310, 410, 510, 610, 710, 910 of the electrosurgical pericardiotomy device 100, 200, 300, 400, 500, 600, 700, 800, 900, 1000, 1100 with the pericardium 10, the tip portion 110, 210, 310, 410, 510, 610, 710, 910 may be positioned proximate the pericardium 10. For example, suitable minimally invasive and/or open surgical access to the pericardium 10 may be obtained using appropriate methods. In some embodiments, the electrosurgical pericardiotomy device 100, 200, 300, 400, 500, 600, 700, 800, 900, 1000, 1100, 2100 may include an elongated shaft 102, 202, 302, 402, 1102, 2102 and the end effector 104, 204 may be disposed distally on the shaft 102, 202, 302, 402, 1102, 2102. Positioning the tip portion 110, 210, 310, 410, 510, 610, 710, 910 proximate the pericardium 10 may include positioning the end effector 104, 204 using the shaft 102, 202, 302, 402, 1102, 2102. In some embodiments, the electrosurgical pericardiotomy device 100, 200, 300, 400, 500, 600, 700, 800, 900, 1000, 1100, 2100 may include a handle 114, 214, 2114 disposed proximally on the shaft 102, 202, 302, 402, 1102, 2102, and positioning the end effector 104, 204 using the shaft 102, 202, 302, 402, 1102, 2102 may include positioning the shaft 102, 202, 302, 402, 1102, 2102 and the end effector 104, 204 using the handle 114, 214, 2114.

In some embodiments, the electrosurgical pericardiotomy device 100, 200, 300, 400, 500, 600, 700, 800, 900, 1000, 1100, 2100 may include at least one vacuum connector 122, 222, 1122 fluidically coupled to the tip portion 110, 210, 310, 410, 510, 610, 710, 910. The vacuum connector 122, 222, 1122 may be fluidically connected to a vacuum source 16.

In some embodiments, the electrosurgical electrode 106, 108, 206, 506, 606, 706, 806, 808, 906, 1006, 1106, 1108, 2106, 2108 may include a monopolar electrosurgical electrode 206, 506, 606, 706, 806, 808, 906, 1006 configured for monopolar operation in connection with a return electrode 240 positioned remotely from the monopolar electrosurgical electrode 206, 506, 606, 706, 806, 808, 906, 1006. Applying electrosurgical energy to the electrosurgical electrode 106, 108, 206, 506, 606, 706, 806, 808, 906, 1006, 1106, 1108 may include applying monopolar electrosurgical energy to the monopolar electrosurgical electrode 206, 506, 606, 706, 806, 808, 906, 1006.

In some embodiments, the electrosurgical electrode 106, 108, 206, 506, 606, 706, 806, 808, 906, 1006, 1106, 1108, 2106, 2108 may include a pair of bipolar electrosurgical electrodes 106, 108, 1106, 1108, 2106, 2108 configured for cooperative bipolar operation. Applying electrosurgical energy to the electrosurgical electrode 106, 108, 206, 506, 606, 706, 806, 808, 906, 1006, 1106, 1108, 2106, 2108 may include applying bipolar electrosurgical energy to the pair of bipolar electrosurgical electrodes 106, 108, 1106, 1108, 2106, 2108.

In some embodiments, the electrosurgical pericardiotomy device 100, 200, 300, 400, 500, 600, 700, 800, 900, 1000, 1100, 2100 may include at least one electrical connector 116, 118, 216, 1116, 2116A, 2116B electrically coupled to the electrosurgical electrode 106, 108, 206, 506, 606, 706, 806, 808, 906, 1006, 1106, 1108, 2106, 2108. The electrosurgical electrode 106, 108, 206, 506, 606, 706, 806, 808, 906, 1006, 1106, 1108, 2106, 2108 may be electrically connected to an electrosurgical generator 14 using the electrical connector 116, 118, 216, 1116, 2116A, 2116B. In some embodiments, a return electrode 240 may be electrically connected to the electrosurgical generator 14, and the return electrode 240 may be positioned for use remotely from the pericardium 10.

In some embodiments, the electrosurgical pericardiotomy device 100, 200, 300, 400, 500, 600, 700, 800, 900, 1000, 1100, 2100 may include an off-the-shelf electrosurgical device electrical connector 1060, 1160 configured to electrically connect with an active electrode 1084 of an off-the-shelf electrosurgical device 1080. The off-the-shelf electrosurgical device electrical connector 1060, 1160 may be electrically coupled to the electrosurgical electrode 106, 108, 206, 506, 606, 706, 806, 808, 906, 1006, 1106, 1108. The off-the-shelf electrosurgical device electrical connector 1060, 1160 may be electrically connected with the active electrode 1084 of the off-the-shelf electrosurgical device 1080 and the off-the-shelf electrosurgical device 1080 may be electrically connected to an electrosurgical generator 14. Applying electrosurgical energy to the electrosurgical electrode 106, 108, 206, 506, 606, 706, 806, 808, 906, 1006, 1106, 1108, 2106, 2108 may include delivering electrical energy to the electrosurgical electrode 106, 108, 206, 506, 606, 706, 806, 808, 906, 1006, 1106, 1108, 2106, 2108 from the electrosurgical generator 14 via the off-the shelf electrosurgical device 1080.

In some embodiments, the off-the-shelf electrosurgical device 1080 may be configured for monopolar operation, and the electrosurgical electrode 106, 108, 206, 506, 606, 706, 806, 808, 906, 1006, 1106, 1108, 2106, 2108 of the electrosurgical pericardiotomy device 100, 200, 300, 400, 500, 600, 700, 800, 900, 1000, 1100, 2100 may include a monopolar electrosurgical electrode 206, 506, 606, 706, 806, 808, 906, 1006 configured for monopolar operation in connection with a return electrode 240 positioned remotely from the monopolar electrosurgical electrode 206, 506, 606, 706, 806, 808, 906, 1006. Delivering electrical energy to the electrosurgical electrode 106, 108, 206, 506, 606, 706, 806, 808, 906, 1006, 1106, 1108, 2106, 2108 from the electrosurgical generator 14 via the off-the shelf electrosurgical device 1080 may include delivering electrical energy from the electrosurgical generator 14 via the off-the-shelf electrosurgical device 1080 to the monopolar electrosurgical electrode 206, 506, 606, 706, 806, 808, 906, 1006.

In some embodiments, the off-the-shelf electrosurgical device 1080 may be configured for monopolar operation, and the electrosurgical electrode 106, 108, 206, 506, 606, 706, 806, 808, 906, 1006, 1106, 1108, 2106, 2108 of the pericardiotomy device 100, 200, 300, 400, 500, 600, 700, 800, 900, 1000, 1100, 2100 may include a pair of bipolar electrosurgical electrodes 106, 108, 1106, 1108 configured for cooperative bipolar operation, the pair of bipolar electrosurgical electrodes 106, 108, 1106, 1108 including a first electrode 106, 1106 and a second electrode 108, 1108. Delivering electrical energy to the electrosurgical electrode 106, 108, 206, 506, 606, 706, 806, 808, 906, 1006, 1106, 1108 from the electrosurgical generator 14 via the off-the shelf electrosurgical device 1080 may include delivering electrical energy from the electrosurgical generator 14 via the off-the-shelf electrosurgical device 14 to the first electrode 106, 1106. In some embodiments, the electrosurgical pericardiotomy device 100, 200, 300, 400, 500, 600, 700, 800, 900, 1000, 1100, 2100 may include an electrical connector 1116, 2116B electrically coupled to the second electrode 108, 1108, 2108. The electrical connector 118, 1116, 2116B may be electrically connected to a return electrode connection 14B of the electrosurgical generator 14.

In some embodiments, the electrosurgical pericardiotomy device 100, 200, 300, 400, 500, 600, 700, 800, 900, 1000, 1100, 2100 may include an electrical connector 2116A electrically coupled to the first electrode 2106. The electrical connector 2116A may be electrically connected to a monopolar connection 14A of the electrosurgical generator 14.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. An electrosurgical pericardiotomy device configured to create an opening through a pericardium, the electrosurgical pericardiotomy device comprising:

an end effector comprising a tip portion of a shaft, the tip portion including a static funnel shape comprising a distal opening configured to engage a target portion of a pericardium, at least a portion of the static funnel shape being translucent, wherein the tip portion is configured, upon application of vacuum thereto, to separate the target portion of the pericardium from an epicardium of a heart; and at least one electrosurgical electrode recessed proximally within the tip portion relative to the distal opening, but visible via the translucent portion of the static funnel shape, so that, with vacuum applied to the tip portion, the target portion of the pericardium contacts the at least one electrosurgical electrode, wherein the at least one electrosurgical electrode is configured to create an opening through the target portion of the pericardium using electrosurgical energy delivered to the at least one electrosurgical electrode.

2. The electrosurgical pericardiotomy device of claim 1, further comprising an elongated shaft;

wherein the end effector is disposed distally on the shaft.

3. The electrosurgical pericardiotomy device of claim 2, wherein the tip portion is formed in a bell shape so that a proximal portion of the tip portion has an outer diameter approximately the same as an outer diameter of the shaft and a distal end of the tip portion has an outer diameter that is substantially greater than the outer diameter of the shaft.

4. The electrosurgical pericardiotomy device of claim 3, wherein the outer diameter of the distal end of the tip portion is about twice the outer diameter of the shaft.

5. The electrosurgical pericardiotomy device of claim 2, further comprising a handle;

wherein the handle is disposed proximally on the shaft.

6. The electrosurgical pericardiotomy device of claim 1, wherein the at least one electrosurgical electrode comprises a monopolar electrosurgical electrode configured for monopolar operation; and wherein the monopolar electrosurgical electrode is configured to be utilized in connection with a return electrode positioned remotely from the monopolar electrosurgical electrode.

7. The electrosurgical pericardiotomy device of claim 1, wherein the at least one electrosurgical electrode comprises a pair of bipolar electrosurgical electrodes configured for cooperative bipolar operation.

8. The electrosurgical pericardiotomy device of claim 1, further comprising an off-the-shelf electrosurgical device electrical connector configured to electrically connect with an active electrode of an off-the-shelf electrosurgical device;

wherein the off-the-shelf electrosurgical device electrical connector is electrically coupled to the at least one electrosurgical electrode so that when the off-the-shelf electrosurgical device is activated, electrical energy is delivered to the at least one electrode of the pericardiotomy device from an electrosurgical generator via the off-the-shelf electrosurgical device.

9. The electrosurgical pericardiotomy device of claim 8, wherein the off-the-shelf electrosurgical device is configured for monopolar operation; and wherein the electrosurgical pericardiotomy device is configured for monopolar operation.

10. The electrosurgical pericardiotomy device of claim 8, wherein the off-the-shelf electrosurgical device is configured for monopolar operation; and wherein the electrosurgical pericardiotomy device is configured for bipolar operation.

11. The electrosurgical pericardiotomy device of claim 10, wherein the at least one electrosurgical electrode comprises a first electrode and a second electrode disposed proximate the tip portion and configured for bipolar operation;

wherein the off-the-shelf electrosurgical device electrical connector is electrically coupled to the first electrode;

wherein the electrosurgical pericardiotomy device further comprises an electrical connector electrically coupled to the second electrode; and wherein the electrical connector is configured to be connected to a return electrode connection of the electrosurgical generator.

12. The electrosurgical pericardiotomy device of claim 1, wherein the at least one electrosurgical electrode comprises a first electrode and a second electrode disposed proximate the tip portion and configured for bipolar operation; and wherein the first electrode is configured to be operatively coupled to a monopolar connection of an electrosurgical generator; and wherein the second electrode is configured to be operatively coupled to a return electrode connection of the electrosurgical generator.

13. The electrosurgical pericardiotomy device of claim 1, further comprising at least one electrical connector electrically coupled to the at least one electrosurgical electrode and configured to electrically connect to an electrosurgical generator.

14. The electrosurgical pericardiotomy device of claim 1, further comprising at least one vacuum connector fluidically coupled to the tip portion and configured to fluidically connect to a vacuum source.

15. An electrosurgical pericardiotomy device configured to create an opening through a pericardium, the electrosurgical pericardiotomy device comprising:

an end effector comprising:

a shaft with a distal tip delineating distal opening, the distal tip configured to engage a target portion of a pericardium, wherein the distal tip is configured, upon application of vacuum to the fixed distal tip, to separate the target portion of the pericardium from an epicardium of a heart; and a first electrode recessed within and extending entirely across a diameter of the distal tip so that, with vacuum applied to the distal tip, the target portion of the pericardium contacts the first electrode, wherein the first electrode is configured to create an opening through the target portion of the pericardium using electrosurgical energy delivered to the first electrode.

16. An electrosurgical pericardiotomy device configured to create an opening through a pericardium, the electrosurgical pericardiotomy device comprising:

an end effector comprising:

a shaft with a distal tip delineating an opening, the distal tip configured to engage a target portion of a pericardium, wherein the distal tip is configured, upon application of vacuum to the distal tip, to separate the target portion of the pericardium from an epicardium of a heart; and a first electrode radially inset from a wall of the distal tip, the first electrode comprising a ring shape, and a second electrode centered within and circumscribed by the first electrode, both recessed within the distal tip so that, with vacuum applied to the distal tip, the target portion of the pericardium contacts the first electrosurgical electrode and the second electrode, wherein the first electrode and the second electrode are configured to create an opening through the target portion of the pericardium using electrosurgical energy delivered to the first electrode and the second electrode.

17. The electrosurgical pericardiotomy device of claim 15, wherein the distal tip includes a rigid funnel shape.

18. The electrosurgical pericardiotomy device of claim 16, wherein the distal tip includes a rigid funnel shape.

\* \* \* \* \*